(12) United States Patent
Hanson et al.

(10) Patent No.: US 8,858,500 B2
(45) Date of Patent: Oct. 14, 2014

(54) ENGAGEMENT AND SENSING SYSTEMS AND METHODS

(75) Inventors: Ian B. Hanson, Northridge, CA (US); Paul F. Bente, IV, South Pasadena, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 272 days.

(21) Appl. No.: 12/650,287

(22) Filed: Dec. 30, 2009

(65) Prior Publication Data

US 2011/0160666 A1 Jun. 30, 2011

(51) Int. Cl.
| | | |
|---|---|---|
| *A61M 1/00* | (2006.01) | |
| *A61M 5/145* | (2006.01) | |
| *A61M 5/172* | (2006.01) | |
| A61M 5/142 | (2006.01) | |
| A61M 5/14 | (2006.01) | |

(52) U.S. Cl.
CPC ... *A61M 5/1456* (2013.01); *A61M 2005/14268* (2013.01); *A61M 5/1723* (2013.01); *A61M 5/1452* (2013.01); *A61M 5/14248* (2013.01); *A61M 5/1413* (2013.01)
USPC .......................................................... 604/151

(58) Field of Classification Search
USPC ............................. 604/151–155, 241, 32, 500
See application file for complete search history.

(56) References Cited

U.S. PATENT DOCUMENTS

| | | |
|---|---|---|
| 3,701,345 A | 10/1972 | Heilman et al. |
| 3,884,230 A | 5/1975 | Wulff |
| 3,994,295 A | 11/1976 | Wulff |
| 4,633,232 A | 12/1986 | Nelson et al. |
| 5,122,123 A | 6/1992 | Vaillancourt |
| 5,236,416 A | 8/1993 | McDaniel et al. |
| 5,334,188 A | 8/1994 | Inoue et al. |
| 5,662,612 A | 9/1997 | Nichoff |
| 5,954,697 A | 9/1999 | Srisathapat et al. |
| 6,283,943 B1 | 9/2001 | Dy et al. |
| 6,299,131 B1 | 10/2001 | Ryan |

(Continued)

FOREIGN PATENT DOCUMENTS

| | | |
|---|---|---|
| DE | 3144825 | 5/1983 |
| EP | 0092712 | 11/1983 |

(Continued)

OTHER PUBLICATIONS

Partial Search Report dated Mar. 1, 2011 from related patent application No. PCT/US2010/060892.

(Continued)

*Primary Examiner* — Jason Flick
(74) *Attorney, Agent, or Firm* — Foley & Lardner LLP

(57) ABSTRACT

A delivery device for delivering fluidic media may include a second housing portion configured to be selectively engaged with and disengaged from a first housing portion adapted to be carried by a user, a drive device configured to be operatively engageable with a plunger arm connected to a plunger head arranged for movement in an axial direction of a reservoir supported by one of the first and second housing portion to drive fluidic media from the reservoir, a drive linkage for operatively engaging the drive device with the plunger arm for allowing the drive device to move the plunger arm, the drive device including a first gear engageable with the plunger arm and a second gear configured for lateral movement to allow the second gear to engage the plunger arm.

51 Claims, 17 Drawing Sheets

(56) References Cited

U.S. PATENT DOCUMENTS

| | | | |
|---|---|---|---|
| 6,423,035 B1 | 7/2002 | Das et al. | |
| 6,699,218 B2 | 3/2004 | Flaherty et al. | |
| 6,740,059 B2 | 5/2004 | Flaherty | |
| 6,749,587 B2 | 6/2004 | Flaherty | |
| 6,945,760 B2 | 9/2005 | Gray et al. | |
| 6,960,192 B1 | 11/2005 | Flaherty et al. | |
| 7,018,360 B2 | 3/2006 | Flaherty et al. | |
| 7,396,353 B2 | 7/2008 | Lorenzen et al. | |
| 7,811,279 B2 * | 10/2010 | John | 604/890.1 |
| 7,935,104 B2 * | 5/2011 | Yodfat et al. | 604/890.1 |
| 8,152,771 B2 | 4/2012 | Mogensen et al. | |
| 8,308,679 B2 | 11/2012 | Hanson et al. | |
| 2001/0034506 A1 | 10/2001 | Hirschman et al. | |
| 2001/0041869 A1 | 11/2001 | Causey et al. | |
| 2004/0002682 A1 | 1/2004 | Kovelman et al. | |
| 2004/0162521 A1 | 8/2004 | Bengtsson | |
| 2005/0065472 A1 | 3/2005 | Cindrich et al. | |
| 2006/0200020 A1 | 9/2006 | Brister et al. | |
| 2007/0049865 A1 | 3/2007 | Radmer et al. | |
| 2007/0060871 A1 | 3/2007 | Istoc et al. | |
| 2007/0073236 A1 | 3/2007 | Mernoe et al. | |
| 2007/0191770 A1 | 8/2007 | Moberg et al. | |
| 2007/0270744 A1 | 11/2007 | Dacquay et al. | |
| 2008/0051697 A1 | 2/2008 | Mounce et al. | |
| 2008/0051711 A1 | 2/2008 | Mounce et al. | |
| 2008/0051714 A1 | 2/2008 | Moberg et al. | |
| 2008/0077081 A1 * | 3/2008 | Mounce et al. | 604/67 |
| 2008/0097321 A1 | 4/2008 | Mounce et al. | |
| 2008/0097328 A1 * | 4/2008 | Moberg et al. | 604/155 |
| 2008/0097381 A1 * | 4/2008 | Moberg et al. | 604/506 |
| 2008/0269687 A1 | 10/2008 | Chong et al. | |
| 2008/0281270 A1 | 11/2008 | Cross et al. | |
| 2008/0319394 A1 * | 12/2008 | Yodfat et al. | 604/154 |
| 2008/0319414 A1 * | 12/2008 | Yodfat et al. | 604/506 |
| 2009/0156990 A1 | 6/2009 | Wenger et al. | |
| 2009/0182301 A1 | 7/2009 | Bassarab et al. | |
| 2009/0259183 A1 | 10/2009 | Chong et al. | |
| 2009/0259198 A1 | 10/2009 | Chong et al. | |
| 2009/0264825 A1 | 10/2009 | Cote | |
| 2009/0326458 A1 | 12/2009 | Chong et al. | |
| 2010/0152658 A1 | 6/2010 | Hanson et al. | |
| 2010/0274180 A1 | 10/2010 | Donovan et al. | |
| 2011/0166512 A1 | 7/2011 | Both et al. | |
| 2011/0178461 A1 | 7/2011 | Chong et al. | |
| 2011/0213306 A1 | 9/2011 | Hanson et al. | |
| 2012/0130312 A1 * | 5/2012 | Mernoe et al. | 604/152 |

FOREIGN PATENT DOCUMENTS

| | | |
|---|---|---|
| EP | 0317808 | 5/1989 |
| EP | 0 937 475 | 8/1999 |
| EP | 1177802 | 2/2002 |
| EP | 1752172 | 2/2007 |
| GB | 2 327 151 | 1/1999 |
| JP | 11-339439 | 12/1999 |
| WO | WO-86/02562 | 5/1986 |
| WO | WO-99/33504 | 7/1999 |
| WO | WO-00/47254 | 8/2000 |
| WO | WO-01/68163 | 9/2001 |
| WO | WO-2006/031500 | 3/2006 |
| WO | WO-2006/076656 | 7/2006 |
| WO | WO-2006/121921 A2 | 11/2006 |
| WO | WO-2006/122406 | 11/2006 |
| WO | WO-2006/124756 | 11/2006 |
| WO | WO-2008/024810 | 2/2008 |
| WO | WO-2008/024812 A2 | 2/2008 |
| WO | WO-2008/024814 A2 | 2/2008 |
| WO | WO-2008/078318 | 7/2008 |
| WO | WO-2008/092782 | 8/2008 |
| WO | WO-2008/133702 | 11/2008 |
| WO | WO-2008/133702 A1 | 11/2008 |
| WO | WO-2009/001346 | 12/2008 |
| WO | WO-2009/016638 | 2/2009 |
| WO | WO-2009/033032 A1 | 3/2009 |
| WO | WO-2009/066288 | 5/2009 |
| WO | WO-2009/098291 A1 | 8/2009 |
| WO | WO-2009/106517 | 9/2009 |
| WO | WO-2009/135667 | 11/2009 |
| WO | WO-2009/144726 A1 | 12/2009 |
| WO | WO-2010/042814 | 4/2010 |
| WO | WO-2011/090629 | 7/2011 |
| WO | WO-2011/119768 | 9/2011 |

OTHER PUBLICATIONS

Partial Search Report dated Mar. 21, 2011 from related patent application No. PCT/US2010/060895.
Partial Search Report dated Mar. 23, 2011 from related patent application No. PCT/US2010/047590.
US Office Action dated Mar. 3, 2011 from related U.S. Appl. No. 12/649,172.
International Search Report and Written Opinion from related patent application No. PCT/US2010/062414.
US Office Action dated Oct. 7, 2010 from related U.S. Appl. No. 12/649,172.
IPRP dated Mar. 6, 2012 from related PCT/US2010/047590 application.
International Search Report and Written Opinion from related PCT application No. PCT/US2011/066501, mailed Dec. 12, 2012, 23 pages.
International Search Report and Written Opinion from related PCT application No. PCT/US2011/066504, mailed Oct. 24, 2012, 29 pages.
International Search Report and Written Opinion from related PCT application No. PCT/US2012/022881, mailed Aug. 28, 2012, 21 pages.
International Search Report and Written Opinion from related PCT application No. PCT/US2012/022883, mailed Aug. 7, 2012, 21 pages.
International Search Report and Written Opinion from related PCT application No. PCT/US2012/055611, mailed Dec. 11, 2012, 11 pages.
U.S. Notice of Allowance from related U.S. Appl. No. 13/235,228, mailed Dec. 20, 2012, 12 pages.
U.S. Non-Final Office Action from related U.S. Appl. No. 12/553,038, mailed Dec. 28, 2012, 10 pages.
U.S. Office Action from related U.S. Appl. No. 12/553,038, mailed Jun. 20, 2013.
U.S. Office Action from related U.S. Appl. No. 13/103,014, mailed May 22, 2013.
International Search Report and Written Opinion from related PCT application No. PCT/US2012/064454, mailed Jun. 12, 2013.
Japanese Office Action from related Japanese Patent Application No. 2012-528022, issued Mar. 25, 2014, 3 pages.
Partial International Search Report from related PCT application No. PCT/US2012/064454, mailed Feb. 4, 2013, 5 pages.
US Office Action dated Jun. 24, 2014, from related U.S. Appl. No. 12/649,172.
US Notice of Allowance dated Jul. 24, 2014, from related U.S. Appl. No. 13/015,028.
US Office Action dated Jul. 1, 2014, from related U.S. Appl. No. 12/974,106.

* cited by examiner

# ENGAGEMENT AND SENSING SYSTEMS AND METHODS

BACKGROUND OF THE INVENTION

1. Field of the Invention

Embodiments of the present invention generally relate to medical device systems and methods, and, in specific embodiments, such systems and methods that include engagement and/or sensing features for engaging and/or sensing parameters associated with components of a medical device system.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have been configured in implantable devices, which are implanted inside of the body of a patient. External pump type delivery devices include devices designed for use in a stationary location, such as a hospital, a clinic, and/or the like, and further include devices configured for ambulatory or portable use, such as devices designed to be carried by a patient, and/or the like. External pump-type delivery devices may contain reservoirs of fluidic media, such as, but is not limited to, insulin.

External pump-type delivery devices may be connected in fluid flow communication to a patient or user-patient, for example, through suitable hollow tubing. The hollow tubing may be connected to a hollow needle that is designed to pierce the skin of the patient and to deliver fluidic media there through. Alternatively, the hollow tubing may be connected directly to the patient as through a cannula, and/or the like.

Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump-type delivery devices may be connected in fluid-flow communication to a patient-user, for example, through suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces skin of the user-patient, a manual insertion of the needle into the patient-user can be somewhat traumatic to the user-patient. Accordingly, insertion mechanisms have been made to assist the insertion of a needle into the user-patient, whereby a needle is forced by a spring to move quickly from a retracted position into an extended position. As the needle is moved into the extended position, the needle is quickly forced through the skin of the user-patient in a single, relatively abrupt motion that can be less traumatic to certain user-patients as compared to a slower, manual insertion of a needle. While a quick thrust of the needle into the skin of the user-patient may be less traumatic to some user-patients than a manual insertion, it is believed that, in some contexts, some user-patients may feel less trauma if the needle is moved at a very slow, steady pace.

Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Pump-type delivery devices can allow accurate doses of insulin to be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump-type delivery devices have become an important aspect of modern medical treatments of various types of medical conditions, such as diabetes. As pump technologies improve and as doctors and patient-users become more familiar with such devices, the popularity of external medical infusion pump treatment increases and is expected to increase substantially over the next decade.

SUMMARY OF THE DISCLOSURE

A delivery device for delivering fluidic media may include, but is not limited to, a first housing portion, a second housing portion, a drive device, and a drive linkage. The first housing portion may be adapted to be secured to a user. The second housing portion may be configured to be selectively engaged with and disengaged from the first housing portion. One of the first housing portion and the second housing portion may be for supporting a reservoir for containing fluidic media. The drive device may be configured to be operatively engageable with a plunger arm connected to a plunger head arranged for movement by the drive device in an axial direction of the reservoir. The drive device may be configured to drive fluidic media from the reservoir in a case where the drive device is operatively engaged with the reservoir and the plunger arm is moved in the axial direction relative to the reservoir. The drive linkage may be operatively engaging the drive device with the plunger arm to allow the drive device to move the plunger arm. The drive linkage may include a first gear and a second gear operatively engaged with each other, the first gear engageable with the plunger arm, the second gear configured for lateral movement such that the lateral movement of the first gear allows the second gear to engage the plunger arm.

In various embodiments, the drive linkage may include a worm and a worm gear operatively engaged with the worm. The worm gear may be for operatively engaging the plunger arm. The worm may have an engagement gear operatively engaged with the drive device such that the worm is movably driven with rotation of the engagement gear by the drive device.

In some embodiments, the first gear may comprise the worm gear. The second gear may comprise the worm and the engagement gear. In some embodiments, the worm and the engagement gear may be integral to each other. In some embodiments, the worm and the engagement gear may comprise plastic.

In various embodiments, the second gear may be supported on a shaft having a longitudinal dimension, the second gear configured to be movable along the longitudinal dimension of the shaft at least between a first position and a second position. In some embodiments, the second gear may be supported on the shaft for rotational movement about an axis of the shaft.

In some embodiments, the second gear may be configured to be slidable along the longitudinal dimension of the shaft. In some, the first gear may be supported on a rotatable shaft for rotational movement about an axis of the rotatable shaft. The first gear may be for operatively engaging the plunger arm to allow the drive device to drive fluidic media from the reservoir in a case where the drive device is operatively engaged with the reservoir and the plunger arm is moved in the axial direction relative to the reservoir.

In further embodiments, the first gear may further include a gear supported on the rotatable shaft for rotational movement about the axis of the rotatable shaft. The gear may be for engaging the plunger arm to allow the drive device to drive fluidic media from the reservoir in a case where the drive device is operatively engaged with the reservoir and the plunger arm is moved in the axial direction relative to the reservoir In yet further embodiments, the gear may have one of threads and teeth. The plunger arm may have one of corresponding threads and teeth for mating with the one of the threads and teeth of the gear upon the one of the threads and teeth of the gear aligning with the one of the corresponding threads and teeth of the plunger arm. The first gear and the plunger arm may be arranged so that the gear engages the plunger arm in a case where the one of the threads and teeth of the gear align with the one of the corresponding threads and teeth of the plunger arm. In yet further embodiments, the gear may comprise a pinion gear.

In further embodiments, at least one of (i) the second gear may be arranged to be at least partially slidable along the shaft to allow the first gear to rotate to an orientation for allowing the first gear to operatively engage the plunger arm and (ii) the first gear may be arranged to be at least partially rotatable about the axial dimension of the rotatable shaft to allow the first gear to rotate to an orientation for allowing the first gear to operatively engage the plunger arm.

In yet further embodiments, the first gear may have one of threads and teeth. The plunger arm may have one of corresponding threads and teeth for mating with the one of the threads and teeth of the first gear upon the one of the threads and teeth of the first gear aligning with the one of the corresponding threads and teeth of the plunger arm. The first gear and the plunger arm may be arranged so that the first gear engages the plunger arm in a case where the one of the threads and teeth of the first gear align with the one of the corresponding threads and teeth of the plunger arm. In yet further embodiments, the first gear may be configured to operatively engage the plunger arm in a case where the first gear and the plunger arm are brought together and the first gear is in a first orientation relative to the plunger arm.

In yet even further embodiments, the first gear may be configured to be movable to the first orientation relative to the plunger arm from a second orientation relative to the plunger arm in a case where the first gear and the plunger arm are brought together and the first gear is in the second orientation relative to the plunger arm. In yet even further embodiments, the first gear may not be engageable with the plunger arm in the second orientation.

In further embodiments, the plunger arm may include at least one of a drive screw and a rack having threads extending along a longitudinal dimension of the rack for operatively engaging with the first gear to allow the drive device to drive fluidic media from the reservoir in a case where the drive device is operatively engaged with the reservoir and the plunger arm is moved in the axial direction relative to the reservoir.

In some embodiments, the second gear may be configured to be movable to the first position to reduce a rotational range of motion of the first gear relative to the plunger arm in a case where the first gear and the plunger arm are engaged and the second gear is in the second position. In further embodiments, the second gear may be configured to be moved to the first position by the drive device. In further embodiments, the delivery device may further include a sensor configured to measure a pressure on the sensor caused by the second gear. In yet further embodiments, the pressure on the sensor caused by the second gear may correspond to a force on the plunger arm. The second gear may contact at least one of the sensor or a structure supporting the sensor in a case where the second gear are in the first position.

In some embodiments, the delivery device may further include a sensor configured to measure a pressure on the sensor caused by the second gear. The pressure on the sensor caused by the second gear may correspond to a force on the plunger arm. In further embodiments, the plunger arm and the first gear may be arranged so that the force on the plunger arm may apply a torque on the first gear. The first gear and the second gear may be arranged to that the torque on the first gear may apply a force on the second gear for applying pressure to the sensor in a case where the second gear is in the second position.

A method of making a delivery device for delivering fluidic media may include, but is not limited to, any one of or combination of: (i) adapting a first housing portion to be secured to a user; (ii) configuring a second housing portion to be selectively engaged with and disengaged from the first housing portion, one of the first housing portion and the second housing portion for supporting a reservoir for containing fluidic media; (iii) configuring a drive device to be operatively engageable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir; (iv) operatively engaging a drive linkage operatively engaged between the drive device and the plunger arm; and (v) providing a drive linkage for operatively engaging the drive device with the plunger arm to allow the drive device to move the plunger arm, the drive linkage including a first gear and a second gear operatively engaged with each other, the first gear engageable with the plunger arm, the second gear configured for lateral movement such that the lateral movement of the first gear allows the second gear to engage the plunger arm.

A delivery device for delivering fluidic media may include a first housing portion, a second housing portion, a drive device, a drive linkage, and a sensor. The first housing portion may be adapted to be secured to a user. The second housing portion may be configured to be selectively engaged with and disengaged from the first housing portion. One of the first housing portion and the second housing portion may be for supporting a reservoir for containing fluidic media. The drive device may be configured to be operatively engageable with a plunger arm connected to a plunger head arranged for movement by the drive device in an axial direction of the reservoir. The drive device may be configured to drive fluidic media from the reservoir in a case where the drive device is operatively engaged with the reservoir and the plunger arm is moved in the axial direction relative to the reservoir. The drive linkage may be for operatively engaging the drive device with the plunger arm to allow the drive device to move the plunger arm. The sensor may be configured to measure a force on the plunger arm.

In various embodiments, the sensor may be configured to measure a linear force of the drive linkage. The linear force of the drive linkage may correspond to the force on the plunger arm. In various embodiments, the force on the plunger arm may be in a direction opposite a direction of movement of the plunger arm to deliver fluidic media from the reservoir.

In various embodiments, the drive linkage may have a first gear operatively engaged with a second gear. The plunger arm and the first gear may be arranged so that the force on the plunger arm may apply a torque on the first gear. The first gear and the second gear may be arranged so that the torque on the first gear may apply the linear force on the second gear. In some embodiments, the first gear may comprise a worm gear. The second gear may comprise a worm.

In some embodiments, the delivery device may further include circuitry for controlling the drive device. The first gear may be operatively engageable with the plunger arm to allow the drive device to move the plunger arm. The circuitry may be configured to control the drive device to move at least one of the first gear and the second gear based on a measurement of the sensor.

In further embodiments, the circuitry may be configured to control the drive device to move the first gear to reduce a rotational range of motion of the first gear relative to the plunger arm. In further embodiments, the circuitry may be configured to control the drive device to move the second gear to reduce a rotational range of motion of the first gear relative to the plunger arm. In yet further embodiments, the circuitry may be configured to control the drive device to move the second gear to reduce the rotational range of motion of the first gear relative to the plunger arm sufficiently to allow the drive device to move the plunger arm.

In further embodiments, the drive device may be controlled to move at least one of the first gear and the second gear by the circuitry based on the force measured by the sensor. In further embodiments, the drive device may comprise an electrical motor.

In various embodiments, the sensor may comprise a force sensor. In various embodiments, the drive device and the reservoir may be operatively engaged in a case where the reservoir is supported by the one of the first housing portion and the second housing portion, the drive device is supported by the other of the first housing portion and the second housing portion, and the first housing portion and the second housing portion are engaged.

In various embodiments, one of the first housing portion and the second housing portion may comprise a disposable housing portion. The other of the first housing portion and the second housing portion may comprise a durable housing portion configured to be selectively engaged with and disengaged from the one of the first housing portion and the second housing portion to allow disposal of the one of the first housing portion and the second housing portion without disposing of the durable housing portion. In various embodiments, the one of the first housing portion and the second housing portion may be for supporting the drive device.

A method of making a delivery device for delivering fluidic media may include, but is not limited to, any one of or combination of: (i) adapting a first housing portion to be secured to a user; (ii) configuring a second housing portion to be selectively engaged with and disengaged from the first housing portion, one of the first housing portion and the second housing portion for supporting a reservoir for containing fluidic media; (iii) configuring a drive device to be operatively engageable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir; (iv) providing a drive linkage for operatively engaging the drive device with the plunger arm to allow the drive device to move the plunger arm; and (v) configuring a sensor to measure a force on the plunger arm.

A method of determining an operating condition of a delivery device, which may have a first housing portion adapted to be secured to a user; a second housing portion configured to be selectively engaged with and disengaged from the first housing portion, one of the first housing portion and the second housing portion for supporting a reservoir for containing fluidic media; a drive device configured to be operatively engageable with a plunger arm connected to a plunger head arranged for movement by the delivery device in an axial direction of the reservoir, circuitry configured to control the drive device to drive fluidic media from the reservoir in a case where the drive device is operatively engaged with the reservoir and the plunger arm is moved in the axial direction relative to the reservoir; and a drive linkage operatively engaged between the drive device and the plunger arm, to allow the drive device to move the plunger arm may include, but is not limited to, any one of or combination of: (i) receiving a plurality of signals or signal parameters, including a first signal or signal parameter representing a first operating condition of the delivery device, a second signal or signal parameter representing a second operating condition of the delivery device, and a third signal or signal parameter representing a third operating condition of the delivery device; (ii) determining with a processor of the delivery device whether each of the plurality of signals or signal parameters meets a respective predetermined parameter; (iii) determining with the processor of the delivery device a result based on whether each of the plurality of signals or signal parameters met the respective predetermined parameter; and (iv) providing a signal based on the result representing the operating condition of the delivery device.

In various embodiments, providing a signal may comprise providing an indication to a user. In various embodiments, the delivery device may be operating properly in a case where each of the plurality of signals or signal parameters meet the respective determined parameter.

In various embodiments, the first signal or signal parameter may correspond to an amount a drive device is controlled to move by the circuitry. In various embodiments, the second signal or signal parameter may correspond to an amount the drive device is moved by the circuitry. In various embodiments, the third signal or signal parameter may correspond to an amount the plunger head is moved.

In various embodiments, the first signal or signal parameter may correspond to an amount a drive device is controlled to move by the circuitry. The second signal or signal parameter may correspond to an amount the drive device is moved by the circuitry. The third signal or signal parameter may correspond to an amount the plunger head is moved.

DETAILED DESCRIPTION OF THE PREFERRED EMBODIMENTS

Figure 1:
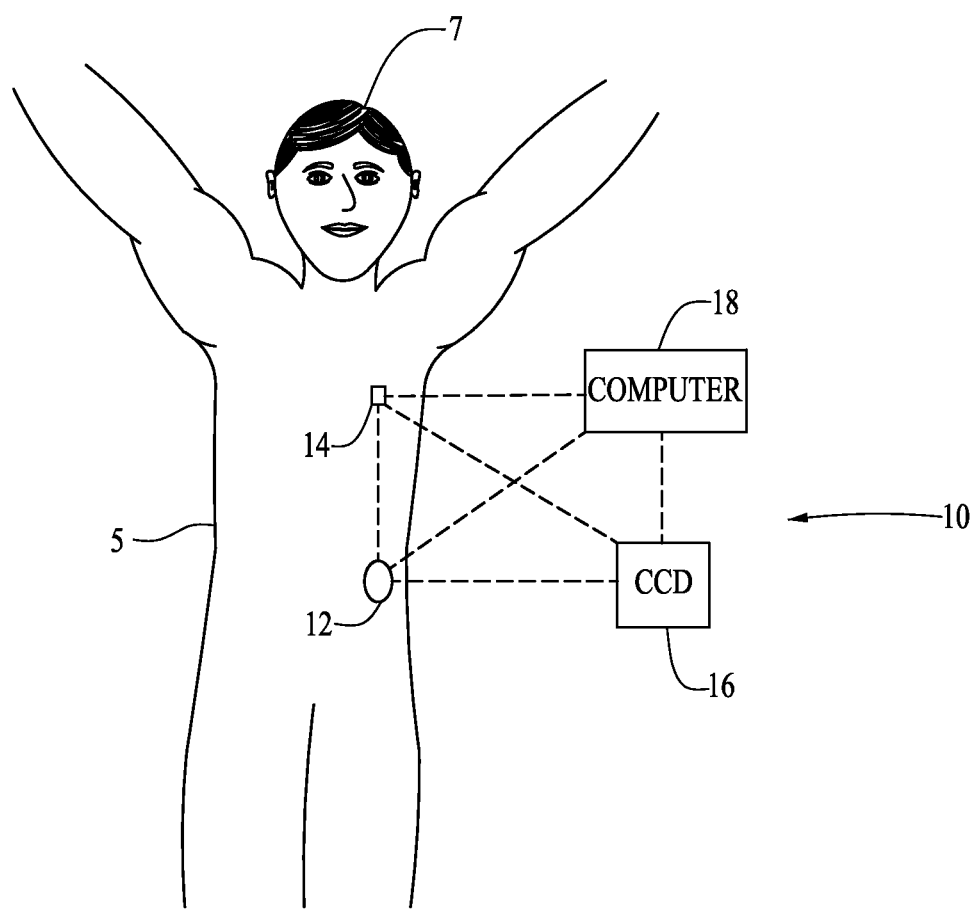
FIG. 1 illustrates a generalized representation of a system in accordance with an embodiment of the present invention.

FIG. 1 illustrates a generalized representation of a system 10 in accordance with an embodiment of the present invention. The system 10 may include a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

The system 10, the delivery device 12, the sensing device 14, the CCD 16, and computer 18 may be similar to those described in the following U.S. Patent Applications that were assigned to the assignee of the present invention, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; (xix) U.S. patent application Ser. No. 11/759,725, filed Jun. 7, 2007, "Infusion Medium Delivery Device And Method With Drive Device For Driving Plunger In Reservoir"; (xx) U.S. patent application Ser. No. 11/606,837, filed Nov. 30, 2006, "Method And Apparatus For Enhancing The Integrity Of An Implantable Sensor Device"; (xxi) U.S. patent application Ser. No. 11/702,713, filed Feb. 5, 2007, "Selective Potting For Controlled Failure And Electronic Devices Employing The Same"; (xxii) U.S. patent application Ser. No. 11/843,601, filed Aug. 22, 2007, "System And Method For Sensor Recalibration"; (xxiii) U.S. patent application Ser. No. 11/868,898, filed Oct. 8, 2007, "Multilayer Substrate"; (xxiv) U.S. patent application Ser. No. 11/964,649, filed Dec. 26, 2007, "System And Methods Allowing For Reservoir Air Bubble Management"; (xxv) U.S. patent application Ser. No. 12/111,751, filed Apr. 29, 2008, "Systems And Methods For Reservoir Filling"; (xxvi) U.S. patent application Ser. No. 12/111,815, filed Apr. 29, 2008, "Systems And Methods For Reservoir Air Bubble Management"; (xxvii) U.S. patent application Ser. No. 11/924,402, filed Oct. 25, 2007, "Sensor Substrate And Method Of Fabricating Same"; (xxviii) U.S. patent application Ser. No. 11/929,428, filed Oct. 30, 2007, "Telemetry System And Method With Variable Parameters"; (xxix) U.S. patent application Ser. No. 11/965,578, filed Dec. 27, 2007, "Reservoir Pressure Equalization Systems And Methods"; (xxx) U.S. patent application Ser. No. 12/107,580, filed Apr. 22, 2008, "Automative Filling Systems And Methods"; (xxxi) U.S. patent application Ser. No. 11/964,663, filed Dec. 26, 2007, "Medical Device With Full Options And Selective Enablement/Disablement"; (xxxii) U.S. patent application Ser. No. 10/180,732, filed Jun. 26, 2002, "Communication Station And Software For Interfacing With An Infusion Pump, Analyte Monitor, Analyte Meter, And/or the like"; (xxxiii) U.S. patent application Ser. No. 12/099,738, filed Apr. 8, 2008, "Systems And Methods Allowing For Reservoir Air Bubble Management"; (xxxiv) U.S. patent application Ser. No. 12/027,963, filed Feb. 7, 2008, "Adhesive Patch Systems And Methods"; (xxxv) U.S. patent application Ser. No. 12/121,647, filed May 15, 2008, "Multi-Lumen Catheter"; (xxxvi) U.S. Patent Provisional Application Ser. No. 61/044,269, filed Apr. 11, 2008, "Reservoir Plunger Head Systems And Methods"; (xxxvii) U.S. Patent Application Ser. No. 61/044,292, filed Apr. 11, 2008, "Reservoir Barrier Layer Systems And Methods"; (xxxviii) U.S. Patent Provisional Application Ser. No. 61/044,322, filed Apr. 11, 2008, "Reservoir Seal Retainer Systems And Methods"; (xxxix) U.S. patent application Ser. No. 12/179,502, filed Jul. 24, 2008, "Method For Formulating And Immobilizing A Matrix Protein And A Matrix Protein For Use In A Sensor"; (xl) U.S. patent application Ser. No. 12/336,367, filed Dec. 16, 2008, "Needle Insertions Systems And Methods"; (xli) U.S. patent application Ser. No. 12/166,210, filed Jul. 1, 2008, "Electronic Device For Controlled Failure"; (xlii) U.S. patent application Ser. No. 12/271,134, filed Nov. 14, 2008, "Multilayer Circuit Devices And Manufacturing Methods Using Electroplated Sacrificial Structures"; (xliii) U.S. patent application Ser. No. 12/171,971, filed Jul. 11, 2008, "Infusion Medium Delivery System, Device And Method With Needle Inserter And Needle Inserter Device And Method"; (xliv) U.S. patent application Ser. No. 12/189,077, filed Aug. 8, 2008, "Packaging System"; (xlv) U.S. patent application Ser. No. 12/179,536, filed Jul. 24, 2008, "Real Time Self-Adjusting Calibration Algorithm"; (xlvii) U.S. patent application Ser. No. 12/277,186, filed Nov. 24, 2008, "Infusion Medium Delivery System, Device And Method With Needle Inserter And Needle Inserter Device And Method"; (xlviii) U.S. patent application Ser. No. 12/211,783, filed Sep. 16, 2008, "Implantable Sensor Method And System"; (xlix) U.S. patent application Ser. No. 12/247,945, filed Oct. 8, 2008, "Infusion Medium Delivery Device And Method With Drive Device For Driving Plunger In Reservoir"; (l) U.S. patent application Ser. No. 12/360,077, filed Jan. 26, 2009, "Reservoir Barrier Layer Systems And Methods"; (li) U.S. patent application Ser. No. 12/345,362, filed Dec. 29, 2008, "Reservoir Seal Retainer Systems And Methods"; (lii) U.S. patent application Ser. No. 12/353,181, filed Jan. 13, 2009, "Systems And Methods Allowing For Reservoir Filling And Infusion Medium Delivery"; and (liii) U.S. patent application Ser. No. 12/360,813, filed Jan. 27, 2009, "Multi-Position Infusion Set Device And Process." In other embodiments, the system 10, delivery device 12, sensing device 14, CCD 16, and computer 18 may have other suitable configurations.

The delivery device 12 may be configured to deliver fluidic media to the body 5 of the user-patient 7. In various embodiments, fluidic media may include a liquid, a fluid, a gel, and/or the like. In some embodiments, fluidic media may include a medicine or a drug for treating a disease or a medical condition. For example, fluidic media may include insulin for treating diabetes, or may include a drug for treating pain, cancer, a pulmonary disorder, HIV, and/or the like. In some embodiments, fluidic media may include a nutritional supplement, a dye, a tracing medium, a saline medium, a hydration medium, and/or the like.

The sensing device 14 may include a sensor, a monitor, and/or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, and/or the like, of the user-patient 7.

In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12. In other embodiments, the sensing device 14 may be separate and apart from the delivery device, and may be, for example, part of the CCD 16. In such embodiments, the sensing device 14 may be configured to receive a biological sample, analyte, and/or the like, to measure a condition of the user-patient 7.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process," all of which are incorporated herein by reference in their entirety.

In such embodiments, the sensing device 14 may be configured to sense a condition of the user-patient 7, such as, but not limited to, blood glucose level, and/or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In some embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. In addition, in various embodiments, the delivery device 12 and/or the sensing device 14 may be configured to transmit data to the CCD 16 and/or the computer 18 for display or processing of the data by the CCD 16 and/or the computer 18.

In some embodiments, the sensing device 14 may be integrated into the CCD 16. Such embodiments may allow the user-patient to monitor a condition by providing, for example, a sample of his or her blood to the sensing device 14 to assess his or her condition. In some embodiments, the sensing device 14 and the CCD 16 may be for determining glucose levels in the blood and/or body fluids of the user-patient without the use of, or necessity of, a wire or cable connection between the delivery device 12 and the sensing device 14 and/or the CCD 16.

In some embodiments, the CCD 16 may be for providing information to the user-patient that facilitates the user-patient's subsequent use of a drug delivery system. For example, the CCD 16 may provide information to the user-patient to allow the user-patient to determine the rate or dose of medication to be administered into the body of the user-patient. In other embodiments, the CCD 16 may provide information to the delivery device 12 to control the rate or dose of medication administered into the body of the user-patient Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same," all of which are incorporated herein by reference in their entirety.

Figure 2:
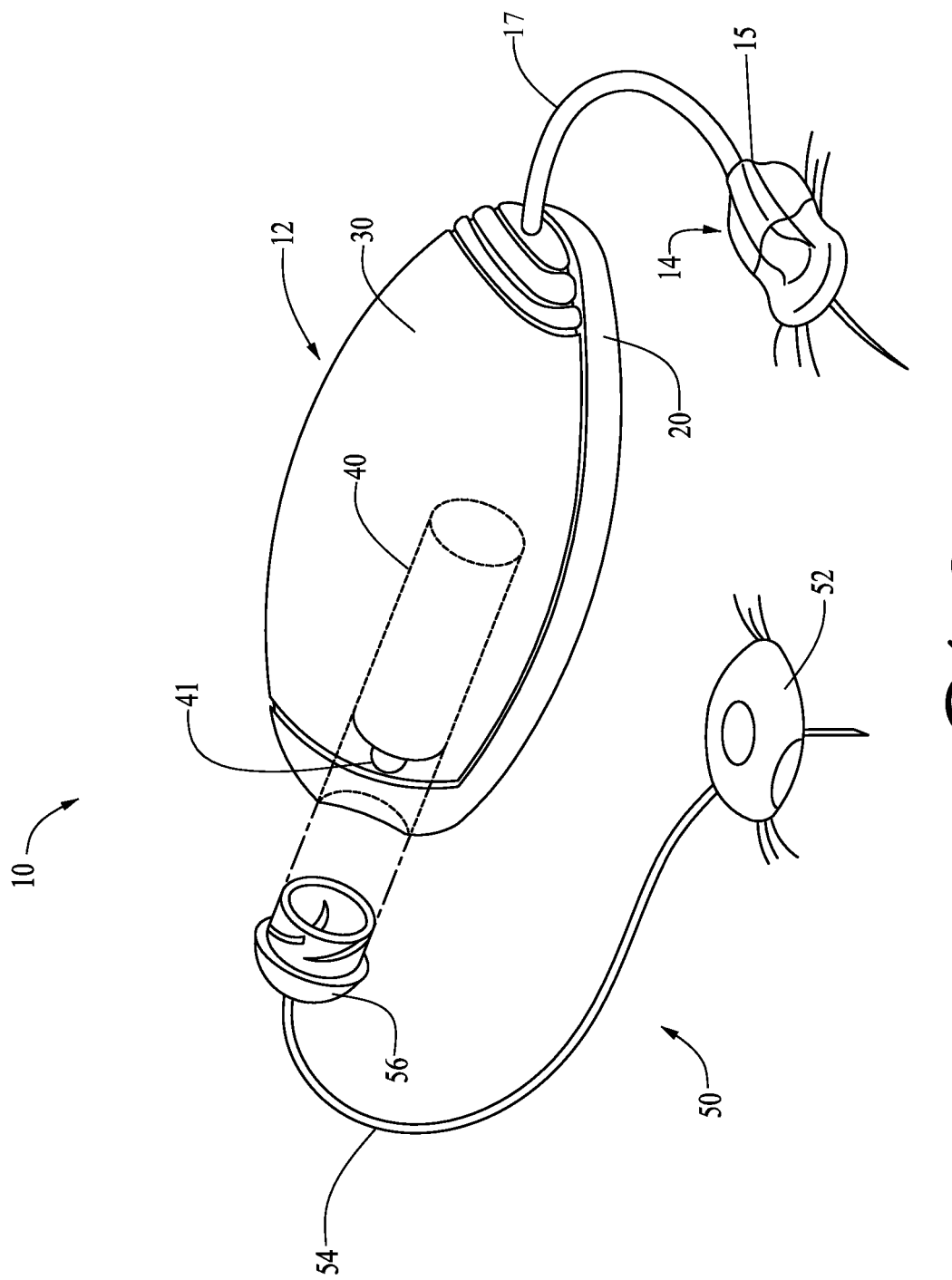
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention may include a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and/or the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 may support the reservoir system 40 and has a bottom surface (facing downward and into the page in FIG. 2) configured to secure to the body of the user-patient. An adhesive may be employed at an interface between the bottom surface of the disposable housing 20 and the skin of the user-patient to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and/or the like. Representative examples of such delivery devices 12, and delivery devices in general, may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 may be configured for containing or holding fluidic media, such as, but not limited to insulin. In various embodiments, the reservoir system 40 may include a hollow interior volume for receiving fluidic media, such as, but not limited to, a cylinder-shaped volume, a tubular-shaped volume, and/or the like. In some embodiments, the reservoir system 40 may be provided as a cartridge or canister for containing fluidic media. In various embodiments, the reservoir system 40 can be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 may include at least one port 41 for allowing fluidic media to flow into and/or flow out of the interior volume of the reservoir system 40. In some embodiments, the infusion path 50 may include a connector 56, a tube 54, and a needle apparatus 52. The connector 56 of the infusion path 50 may be connectable to the port 41 of the reservoir system 40. In various embodiments, the disposable housing 20 may be configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 may be covered with or supports a septum (not shown in FIG. 2), such as a self-sealing septum, and/or the like. The septum may be configured to prevent fluidic media from flowing out of the reservoir system 40 through the port 41 when the septum is not pierced. In addition, in various embodiments, the connector 56 of the infusion path 50 may include a needle for piercing the septum covering the port 41 of the reservoir system 40 to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector," which is incorporated herein by reference in its entirety. In other alternatives, non-septum connectors such as Luer locks, and/or the like may be used. In various embodiments, the needle apparatus 52 of the infusion path 50 may include a needle that is able to puncture the skin of the user-patient. In addition, in various embodiments, the tube 54 connects the connector 56 with the needle apparatus 52 and may be hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features that allow the two parts to connect together easily, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20 to provide a seal against water entering between the durable housing 30 and the disposable housing 20.

The durable housing 30 of the delivery device 12 may support a drive device (not shown in FIG. 2) that may include a motor and a drive device linkage portion. The drive device may be configured to apply a force to fluidic media within the reservoir system 40 to force fluidic media out of the reservoir system 40 and into an infusion path, such as the infusion path 50, for delivery to a user-patient. For example, in some embodiments, an electrically-driven motor 84 (refer to FIGS. 5B and 5C) may be mounted within the durable housing 30 with appropriate linkage for operatively coupling the motor 84 to a plunger arm (refer to FIGS. 6A-6C) connected to a plunger head (refer to FIGS. 6A-6C) arranged within the reservoir system 40. The electrically-driven motor may be configured to drive the plunger head in a direction to force fluidic media out of the port 41 of the reservoir system 40 and to the user-patient.

Also, in some embodiments, the motor 84 may be controllable to reverse direction to move the plunger arm 60 and the plunger head to cause fluid to be drawn into the reservoir system 40 from a patient. The motor 84 may be arranged within the durable housing 30 and the reservoir system 40 may be correspondingly arranged on the disposable housing 20, such that the operable engagement of the motor 84 with the plunger head, through the appropriate linkage, occurs automatically upon the user-patient connecting the durable housing 30 with the disposable housing 20 of the delivery device 12. Further examples of linkage and control structures may be found in, but are not limited to, U.S. patent application Ser. No. 09/813,660, filed Mar. 21, 2001, entitled "Control Tabs for Infusion Devices and Methods of Using the Same"; U.S. Patent Pub. No. 2006/0264894 (Ser. No. 11/211,095), filed Aug. 23, 2005, entitled "Infusion Device and Method with Disposable Portion"; U.S. patent application Ser. No. 11/210,467, filed Aug. 23, 2005, entitled "Infusion Device and Method With Drive In Separable Durable Housing Portion"; U.S. patent application Ser. No. 11/211,150, filed Aug. 23, 2005, entitled "Pump Assembly and Method For Infusion Device"; U.S. patent application Ser. No. 11/210,455, filed Aug. 23, 2005, entitled "Reservoir Support And Method For Infusion Device"; and U.S. Pat. No. 6,485,465, filed Mar. 27, 2001, entitled "Methods, Apparatuses, and Uses for Infusion Pump Fluid Pressure and Force Detection," all of which are incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, and/or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, and/or the like. By forming the disposable housing 20 of a material capable of flexing with the skin of a user-patient, a greater level of user-patient comfort may be achieved when the disposable housing 20 is secured to the skin of the user-patient. In addition, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 17 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, and/or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set," which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level and/or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 may include a sensor 15 connected by the connection element 17 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
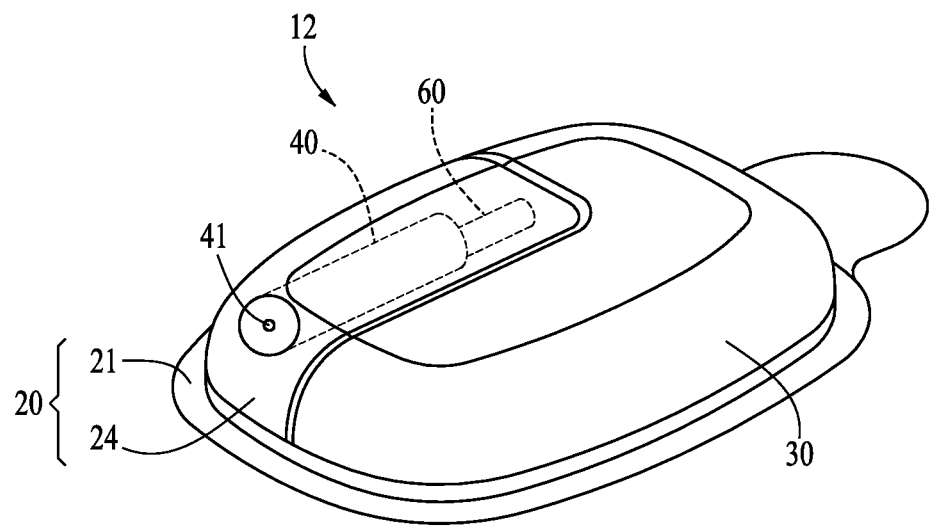
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 may be configured to be securable to a body of a user-patient. The reservoir-retaining portion 24 of the disposable housing 20 is configured to house the reservoir system 40. The reservoir-retaining portion 24 of the disposable housing 20 may be configured to have an opening to allow for the port 41 of the reservoir system 40 to be accessed from outside of the reservoir-retaining portion 24 while the reservoir system 40 is housed in the reservoir-retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
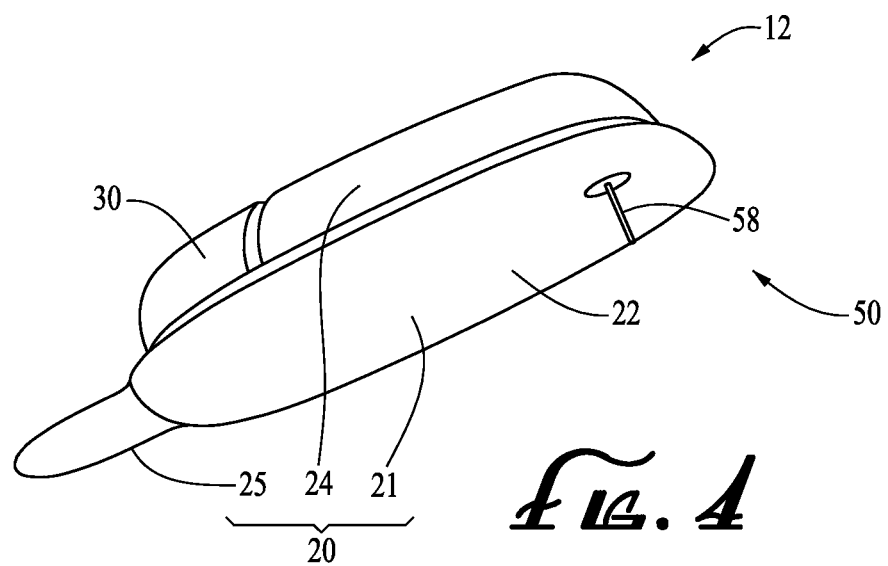
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir-retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place with one end of the cannula located within the body of the user-patient and the other end of the cannula in fluid flow connection with fluidic media within the reservoir system 40. Accordingly, fluidic media may be conveyed from the reservoir system 40 to the body of the user-patient.

Figure 5A:
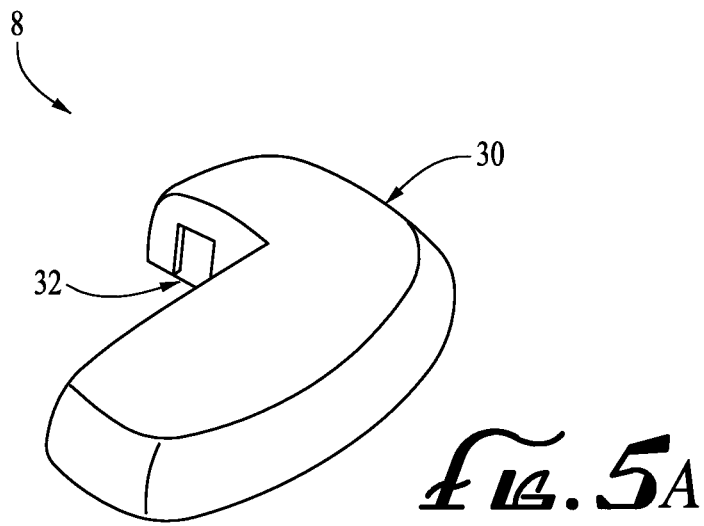
FIG. 5A illustrates a durable portion of a delivery device in accordance with an embodiment of the present invention.
Figure 5B:
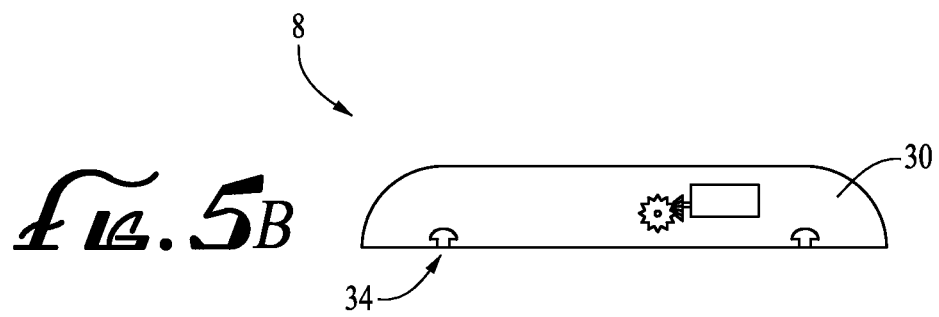
FIG. 5B illustrates a section view of a durable portion of a delivery device in accordance with an embodiment of the present invention.
Figure 5C:
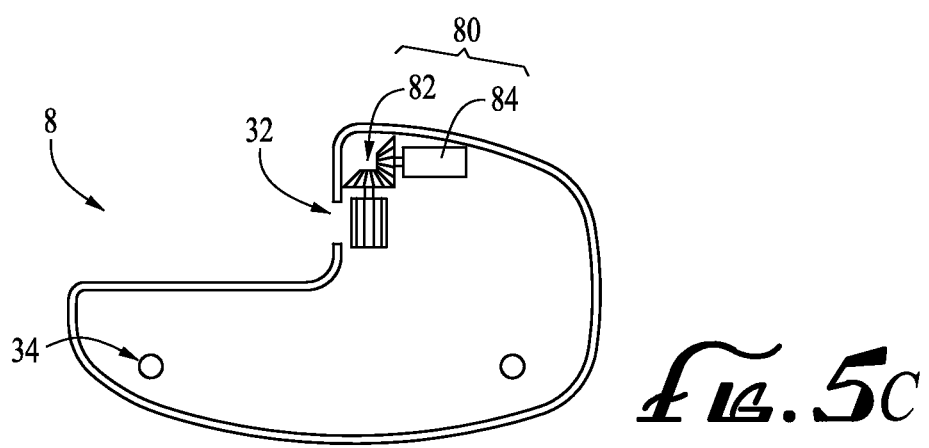
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 may include the durable housing 30, and a drive device 80. The drive device 80 may include a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). In addition, in various embodiments, the durable housing 30 may be configured with an opening 32 for receiving a plunger arm 60 (refer to FIG. 3). In addition, in various embodiments, the durable housing 30 may include one or more connection members 34, such as tabs, insertion holes, and/or the like, for connecting with the base 21 of the disposable housing 20 (refer to FIG. 3).

Figure 6A:
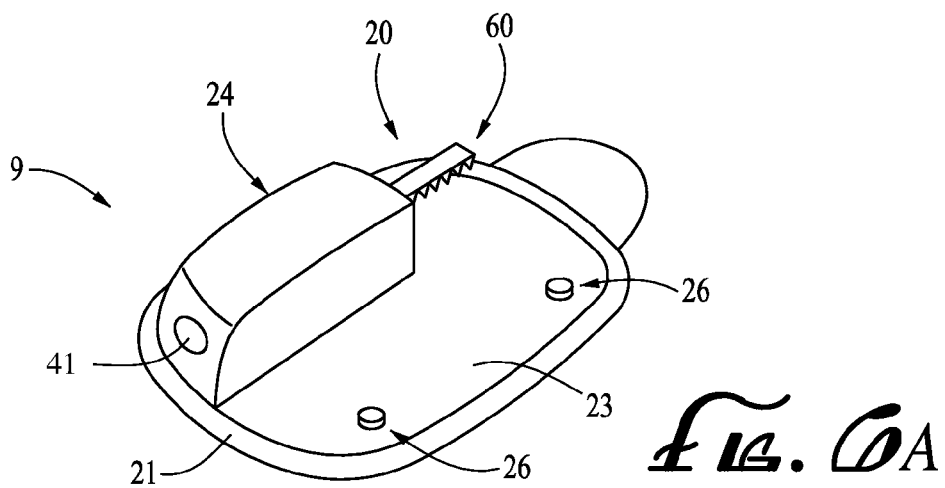
FIG. 6A illustrates a disposable portion of a delivery device in accordance with an embodiment of the present invention.
Figure 6B:
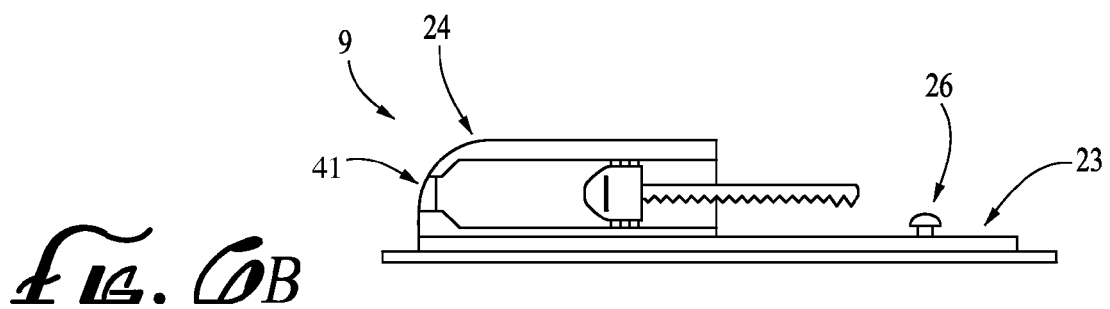
FIG. 6B illustrates a section view of a disposable portion of a delivery device in accordance with an embodiment of the present invention.
Figure 6C:
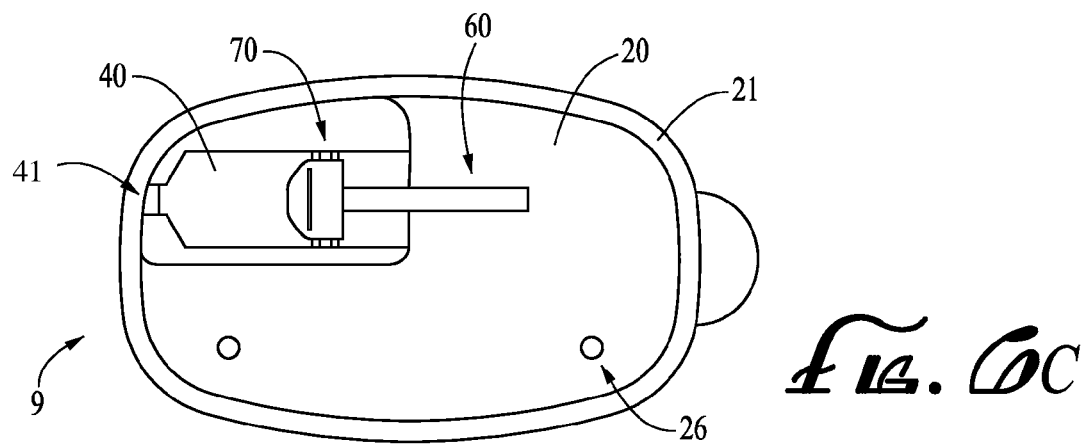
FIG. 6C illustrates a section view of a disposable portion of a delivery device in accordance with an embodiment of the present invention.
Figure 7:
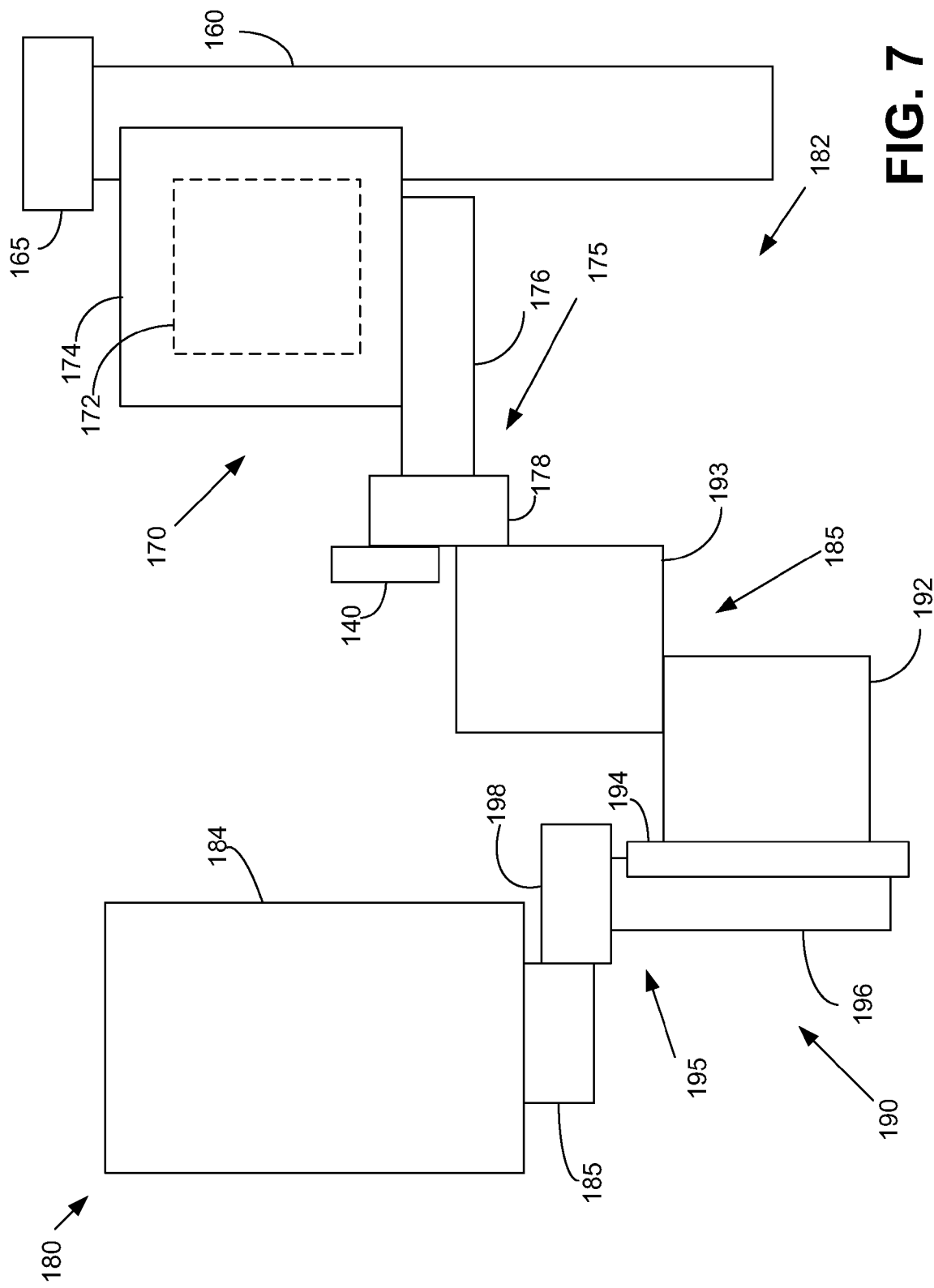
FIG. 7 illustrates a portion of a medical device system in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. The plunger head 70 may be made of Bromobutyl rubber, silicone rubber, or any other suitable material and/or any derivative thereof. In some embodiments, the disposable housing 20 may include the base 21 and the reservoir-retaining portion 24. In various embodiments, the base 21 may include a top surface 23 having one or more connection members 26, such as tabs, grooves, and/or the like, for allowing connections with the one or more connection members 34 of embodiments of the durable housing 30 (refer to FIG. 5B).

In various embodiments, the reservoir system 40 may be housed within the reservoir retaining portion 24 of the disposable housing 20, and the reservoir system 40 may be configured to hold fluidic media. In addition, in various embodiments, the plunger head 70 may be disposed at least partially within the reservoir system 40 and may be movable within the reservoir system 40 to allow fluidic media to fill into the reservoir system 40 and to force fluidic media out of the reservoir system 40. In some embodiments, the plunger arm 60 may be connected to or is connectable to the plunger head 70.

Also, in some embodiments, a portion of the plunger arm 60 may extend to outside of the reservoir-retaining portion 24 of the disposable housing 20. In various embodiments, the plunger arm 60 may have a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82. Accordingly, the plunger arm 60 may be moved to cause the plunger head 70 to move within the reservoir system 40. When the interior volume of the reservoir system 40 is sufficiently filled with fluidic media and an infusion path is provided from the reservoir system 40 to the body of the user-patient, the plunger head 70 may be moved within the reservoir system 40 to force fluidic media from the reservoir system 40 to the user-patient via the infusion path.

In various embodiments, once the reservoir system 40 has been sufficiently emptied or otherwise requires replacement, the user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. In addition, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 may include reservoir status circuitry (not shown), and the reservoir system 40 may include reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; (iv) an amount of contents in the reservoir system 40; and/or the like. In some embodiments, the delivery device 12 may include the reservoir status circuitry, and the reservoir status circuitry may be configured to read data from the reservoir circuitry when the reservoir system 40 is inserted into the disposable portion 9.

In various embodiments, the reservoir status circuitry may be further configured to store data to the reservoir circuitry after at least some of the contents of the reservoir system 40 have been transferred out of the reservoir system 40 to update information in the reservoir circuitry. Such information may be related to, but is not limited to, an amount of fluidic media remaining in the reservoir system 40, an amount of fluidic media already delivered, plunger head 60 location, pressure within the reservoir system 40, and/or the like.

In some embodiments, the reservoir status circuitry may be configured to store data to the reservoir circuitry to update information in the reservoir circuitry related to an amount of contents remaining in the reservoir system 40 when the reservoir system 40 is inserted into the disposable portion 9. In some embodiments, the delivery device 12 may include the reservoir status circuitry and the reservoir system 40 may include the reservoir circuitry, and the reservoir status circuitry may selectively inhibit use of the delivery device 12 or may selectively provide a warning signal based on information read by the reservoir status circuitry from the reservoir circuitry.

In various embodiments, any of the connection structure described above for allowing one or more parts of the delivery device to be selectively connectable to and separable from one or more other parts of the delivery device may include one or more elements as will be described. The element(s) may function to provide one or more of aligning connectable parts, connection of connectable parts, and sensing the connection of connectable parts, as will be described.

FIGS. 7-18 illustrates a drive device system 180 according to an embodiment of the present invention. The drive device system 180 may include features similar to the medical device systems or portions thereof (e.g., drive device 80 in FIGS. 1-6C) discussed throughout the disclosure or employed as an embodiment of the medical devices (e.g., delivery device 12 in FIGS. 1-6C) discussed throughout the disclosure. In addition, some or all of the features shown in FIGS. 1-6C may be combined in various ways and included in the embodiments shown in FIGS. 7-18. Likewise, it should be understood that any of the features of the embodiments of FIGS. 7-18 may be combined or otherwise incorporated into any of the other embodiments of FIGS. 7-18 as well as any other embodiment herein discussed.

The drive device system 180 may include a motor 184, which may be similar to the motor 84 (e.g., FIGS. 1-6C), and a drive device linkage portion 182, which may be similar to the drive device linkage portion 82 (e.g., FIGS. 1-6C). The motor 184 may be controlled to drive the drive device linkage portion 182. In some embodiments, for example, the motor 184 may include a motor gear 185 supported on a rotary shaft 181 (e.g., FIG. 8). The rotary shaft 181 may be driven by the motor 184 to rotate or otherwise move the motor gear 185. Thus in some embodiments, the motor gear 185 may be arranged to operatively engage with the drive device linkage portion 182 to allow the motor 184 to drive the drive device linkage portion 182 via the motor gear 185.

Figure 16:
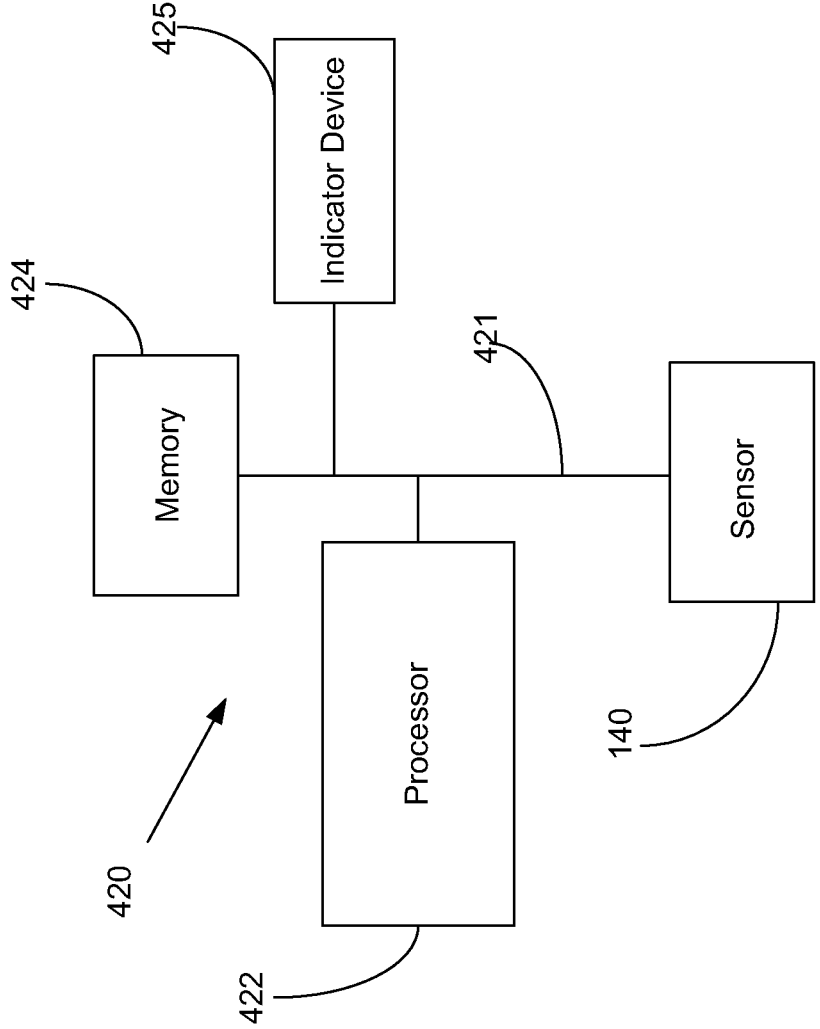
FIG. 16 illustrates a portion of a medical device system in accordance with an embodiment of the present invention.
Figure 17:
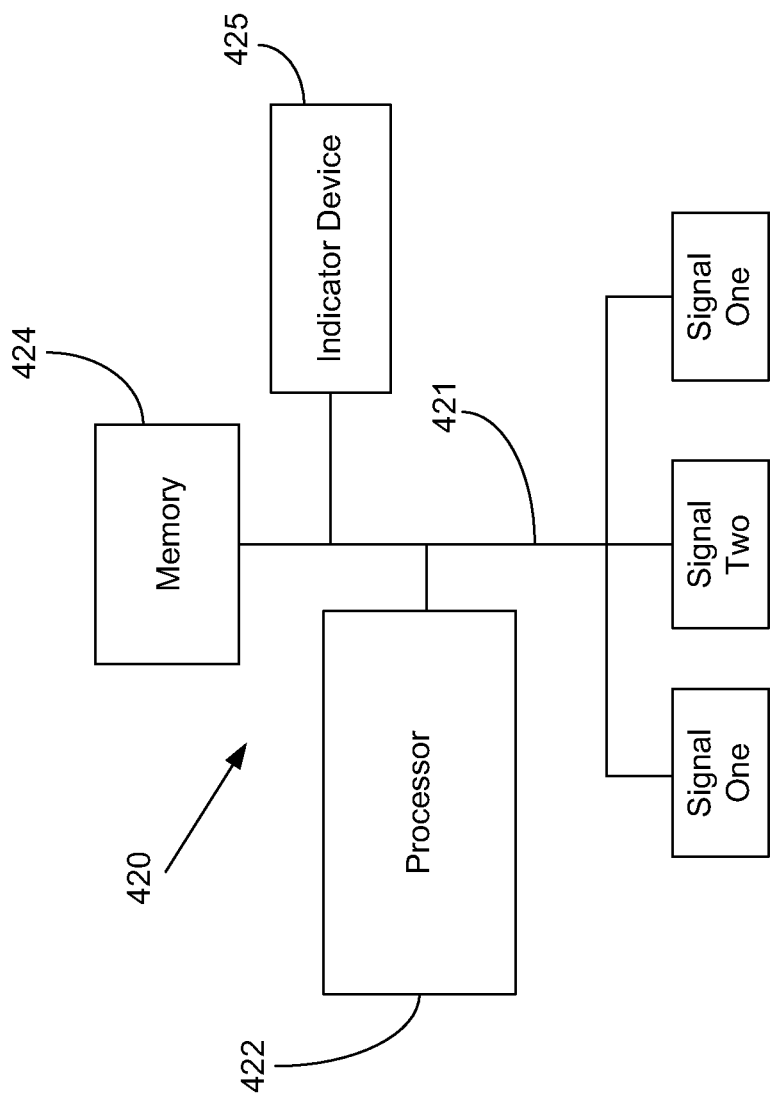
FIG. 17 illustrates a portion of a medical device system in accordance with an embodiment of the present invention.

In various embodiments, the motor 184 may be provided with electrical terminals for connection to a motor control circuit 420 (e.g., FIGS. 16-17). The motor control circuit 420 may be mounted within the durable portion 22 (e.g., FIG. 1-6C) of the delivery device 12 (e.g., FIG. 1-6C) for controlling operation of the motor 184 according to a desired infusion delivery program or profile. In other embodiments, the motor control circuit 420 may be mounted in the disposable portion 20 and connectable to the electrical terminals of the motor 184 when the durable portion 22 and the disposable portion 20 are engaged and connected together.

A delivery program or profile may be stored within a suitable electronic storage medium (e.g., memory 424 in FIGS. 16 and 17) located within the durable portion 22 and/or may be communicated to the delivery device 12 from other sources, such as a CCD 16 or a computer 18 (e.g., FIG. 1-6C). Alternatively or in addition, the motor control circuit 420 may control the motor 184 to deliver one or more discrete volumes of infusion media in response to delivery demand control signals generated within the delivery device 12 or communicated to the delivery device 12 from other sources, such as a CCD 16 or a computer 18. The motor 184 may be, but is not limited to, a step motor, DC motor, voice coil motor, three-phase motor, and/or the like.

The drive device linkage portion 182 may be configured to engage or mate with a plunger arm 160 (e.g., FIG. 7) having a plunger head 165, each of which may be similar to, but is not limited to, the plunger arm 60 and the plunger head 70 (e.g., FIGS. 1-6C) previously described. Accordingly, the plunger arm 160 may be moved by the motor 184 via the drive device linkage portion 182 to move the plunger head 165 within a reservoir 168. The reservoir 168 may be similar to, but is not limited to, the reservoir system 40 (e.g., FIGS. 1-6C).

In some embodiments, the drive device linkage portion 182 may be configured to control engagement of the drive device linkage portion 182 to the plunger arm 160. For example, the drive device linkage portion 182 may be configured to substantially remove or otherwise control slack between the plunger arm 160 and one or more gears of the drive device linkage portion 182 and/or between gears of the drive device linkage portion 182, as will be described. In various embodiments, slack may be a range of rotational motion of one or more gears relative to, for example, the plunger arm 160. The range of rotational motion, which may be, for example, but is not limited to, thirty degrees in a clockwise and/or counter-clockwise direction may provide the gear with sufficient freedom of movement (or rotation) to allow threads, teeth, or the like of the gear to align and mate (or "mesh") with corresponding threads, teeth, or the like on the plunger arm 160. In further embodiments, as will be described later in greater detail, the slack or the range of rotational motion may be sufficiently reduced, for example (but not limited to) near zero, to increase engagement of the various gears in the drive device linkage portion 182. Accordingly, in a case where the drive device linkage portion 182 is operatively engaged with the plunger arm 160 and the range of rotational motion (or slack) of a particular gear (or gears) has been sufficiently reduced, a drive force provided by the motor 184 may be transferred along each of the gears of the drive device linkage portion 182 to the plunger arm 160 more efficiently than in a case where slack is not reduced.

In some embodiments, the drive device linkage portion 182 may include a first linkage portion 170. The first linkage portion 170 may include a worm drive or other arrangement, for example, configured to allow torque to be transmitted between gears. In such embodiments, the first linkage portion 170 may include a first worm gear (or worm wheel) 174 arranged to engage with a complementing gear, such as a first worm 176, or the like. The first worm 176 and/or the first worm gear 174 may be made of any suitable material, such as, but not limited to, plastic (e.g., carbon fiber impregnated plastic), metal, composite materials, and/or the like. In particular embodiments, the first worm 176 may be supported and/or rotatable about an axis perpendicular to an axis supporting the first worm gear 174.

The first worm 176 may be operatively engaged or otherwise connected with a first engagement gear 178 (e.g., pinion gear, spur gear, and/or the like) such that the first engagement gear 178 and the first worm 176 have a shared axis of rotation. Thus, the first engagement gear 178 may be supported and/or rotatable about the axis perpendicular to the axis supporting the first worm gear 174. The first engagement gear 178 may be made of any suitable material, such as, but not limited to, plastic, metal, composite materials, and/or the like.

The first engagement gear 178 and the first worm 176 may be supported on a first shaft 171 (e.g., FIG. 8) to allow rotational movement of the first engagement gear 178 and the first worm 176 about the first shaft 171. In some embodiments, the first shaft 171 may be supported or integrated with a structure 152. The first engagement gear 178 may be arranged to operatively engage (e.g., via a second linkage portion 190 and/or the like) with the motor gear 185 to allow the motor 184 to drive the first linkage portion 170.

In some embodiments, the first worm 176 and the first engagement gear 178 may be integral with each other to form a worm body 175. The worm body 175 may be made of any suitable material, such as, but not limited to, plastic, metal, composite materials, and/or the like. In some embodiments, the worm body 175 may be made of a material different from some of gears operatively engaged with the worm body 175. In particular embodiments where the worm body 175, portions thereof (e.g., the first worm 176 or the engagement gear 178), and/or other gears is/are made of plastic or the like, noise created from engagement and motion of the gears may be reduced.

In further embodiments, the first engagement gear 178 and the first worm 176 may be arranged on the first shaft 171 to allow movement along a longitudinal dimension of the first shaft 171 at least between a first position 171a and a second position 171b, for example, as the first engagement gear 178 is driven by the motor 184. In particular embodiments, the first engagement gear 178 and the first worm 176 may be configured to be slidable along the longitudinal dimension of the first shaft 171 at least between the first position 171a and the second position 171b, for example, as the first engagement gear 178 is driven by the motor 184, or to allow the first linkage portion 170 to "mesh" or otherwise operatively engage with the plunger arm 160.

In various embodiments, by configuring the first engagement gear 178 and the first worm 176 to be slidable along the first shaft 171, a sliding motion of the first engagement gear 178 and the first worm 176 may provide the first worm gear 174, which may be engaged with the first worm 176, a range of rotational motion (or slack), for example, the plunger arm 160. The range of rotational motion, which may be, for example, but is not limited to, thirty degrees in a clockwise and/or counterclockwise direction may provide the first worm gear 174 with sufficient freedom of movement (or rotation) to allow threads, teeth, or the like of the first worm gear 174 (and/or other gear, such as gear 172, sharing an axis with the first worm gear 174) to align and mate (or "mesh") with corresponding threads, teeth, or the like on the plunger arm 160. In further embodiments, as will be described later in greater detail, the slack or the range of rotational motion may be sufficiently reduced, for example (but not limited to) near zero, to increase engagement of the first worm gear 174 (and/or other gear sharing an axis with the first worm gear 164) with the plunger arm 160. Accordingly, in a case where the drive device linkage portion 182 is operatively engaged with the plunger arm 160 and the range of rotational motion (or slack) of the first worm gear 174 (and/or other gear sharing an axis with the first worm gear 164) has been sufficiently reduced, a drive force provided by the motor 184 may be transferred along each of the gears of the drive device linkage portion 182 to the plunger arm 160 more efficiently than in a case where slack is not reduced.

In some embodiments, the first position 171a may correspond to a position at which an end 175b of the worm body 175 contacts the structure 152 (or component thereof). The second position 171b may correspond to a position at which an end 175a, which may be opposite the end 175b, of the worm body 175 contacts the structure 152 (or component thereof) (e.g., FIG. 8). The first shaft 171 may be made of any suitable material, such as, but not limited to, plastic, metal, composite materials, and/or the like.

Figure 8:
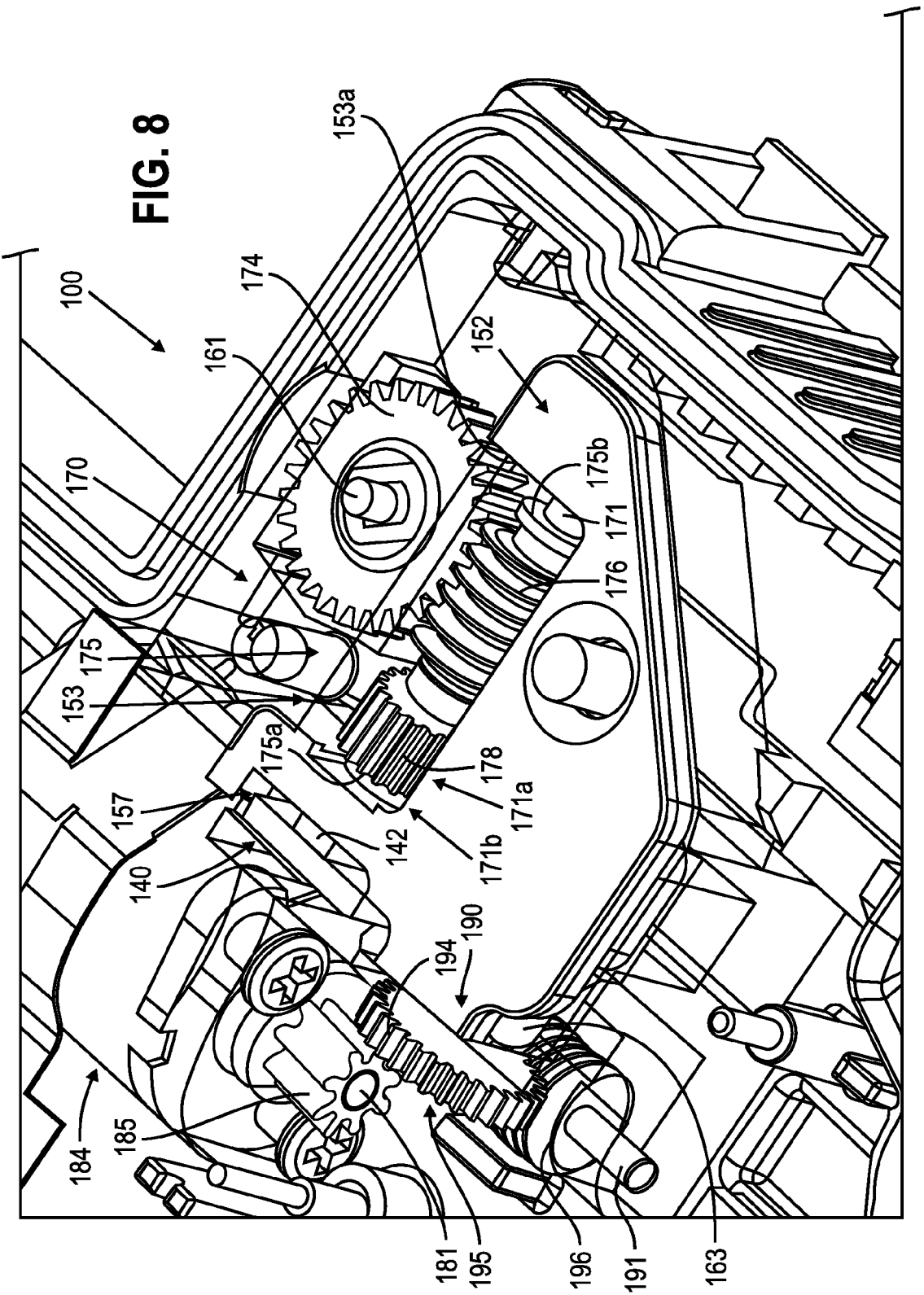
FIG. 8 illustrates a portion of a medical device system in accordance with an embodiment of the present invention.
Figure 9:
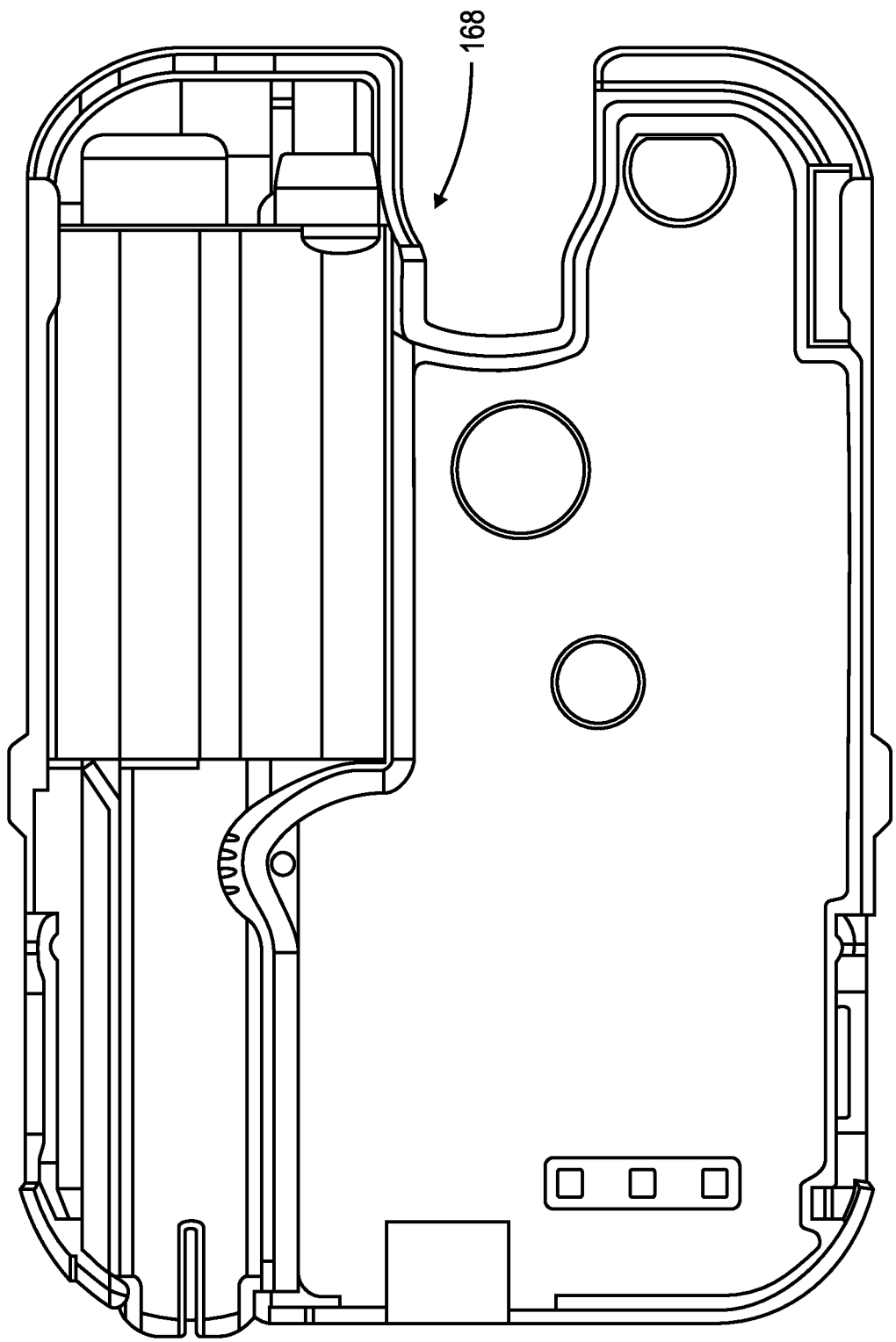
FIG. 9 illustrates a portion of a medical device system in accordance with an embodiment of the present invention.
Figure 10:
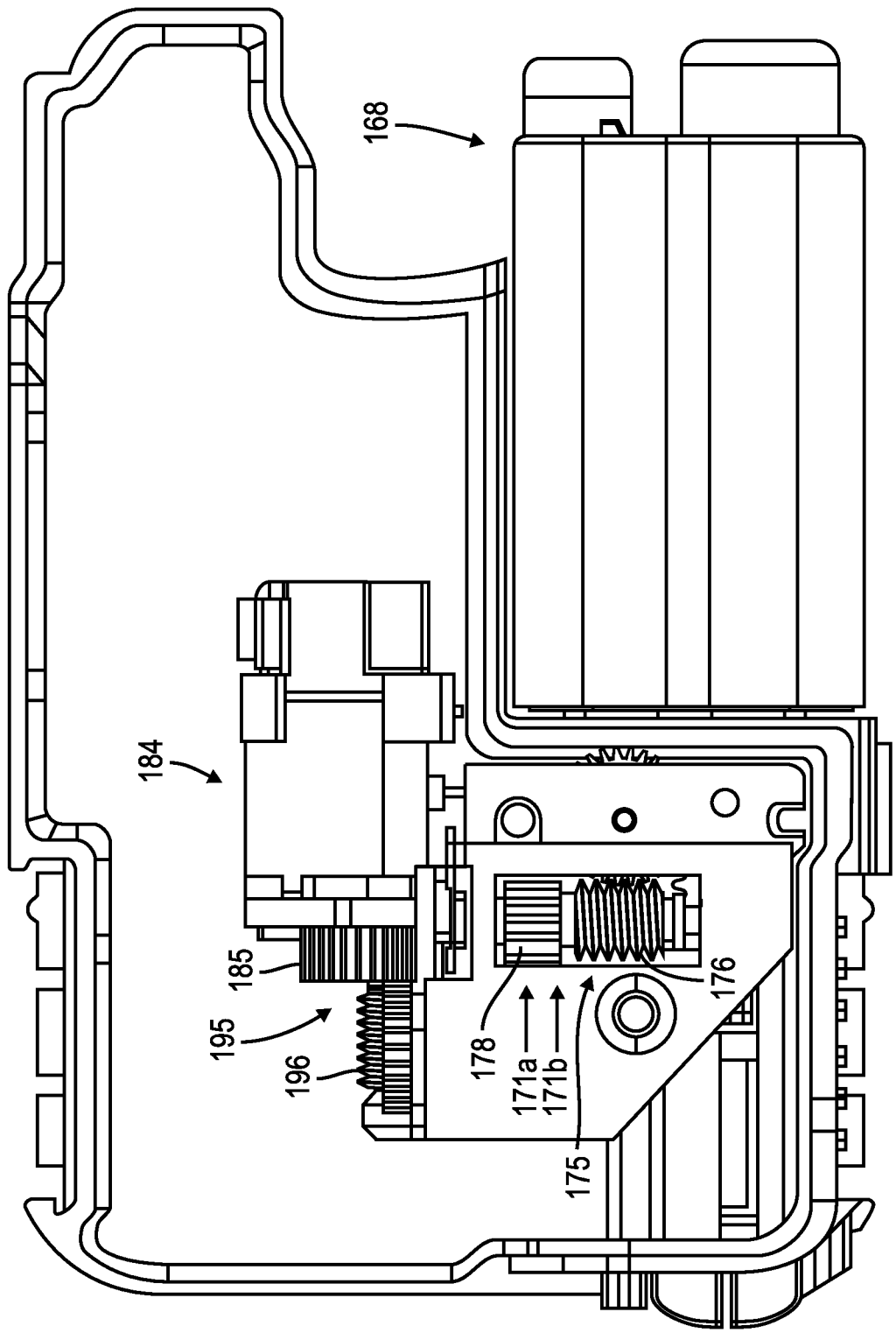
FIG. 10 illustrates a portion of a medical device system in accordance with an embodiment of the present invention.
Figure 11:
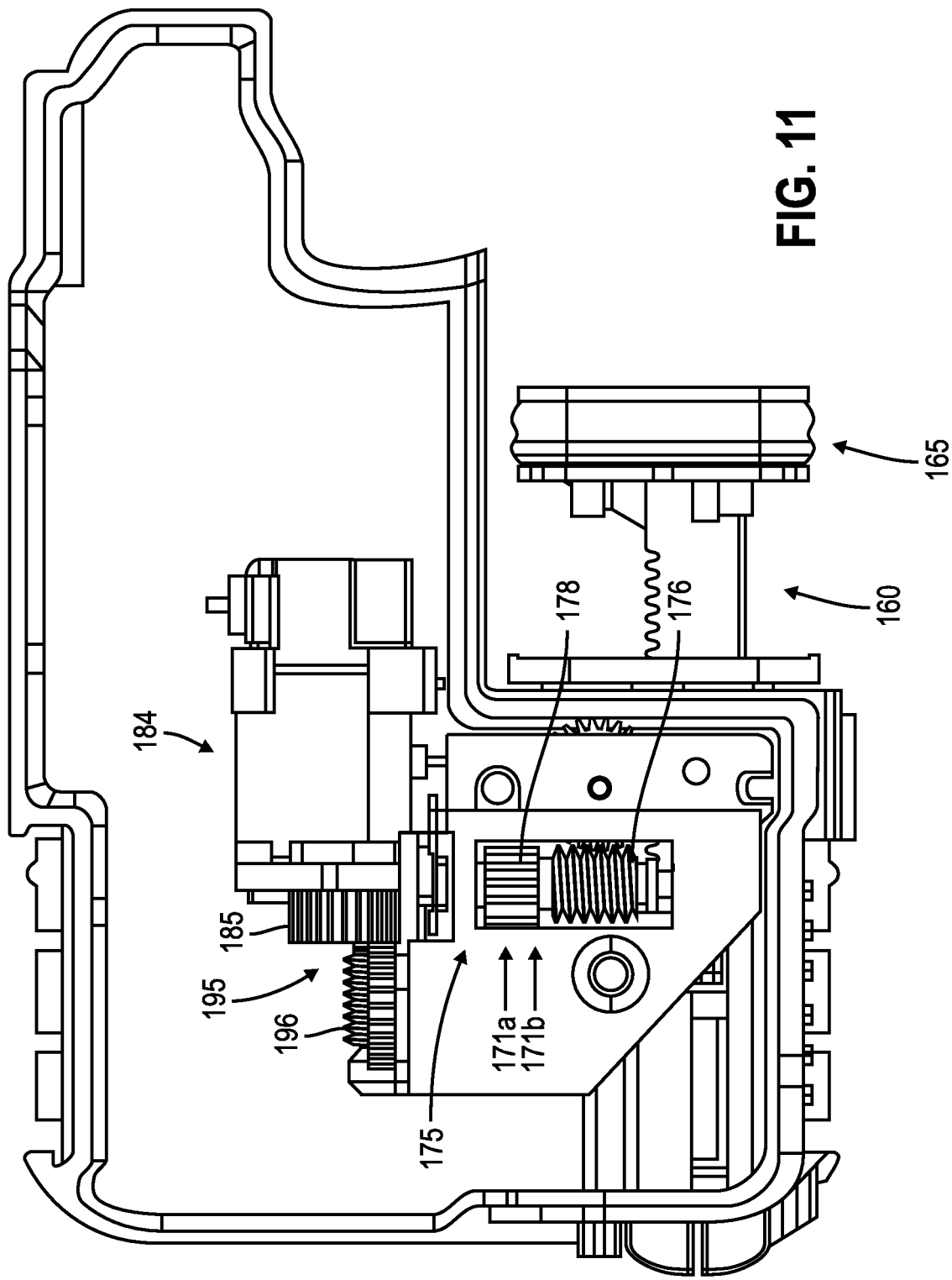
FIG. 11 illustrates a portion of a medical device system in accordance with an embodiment of the present invention.
Figure 12:
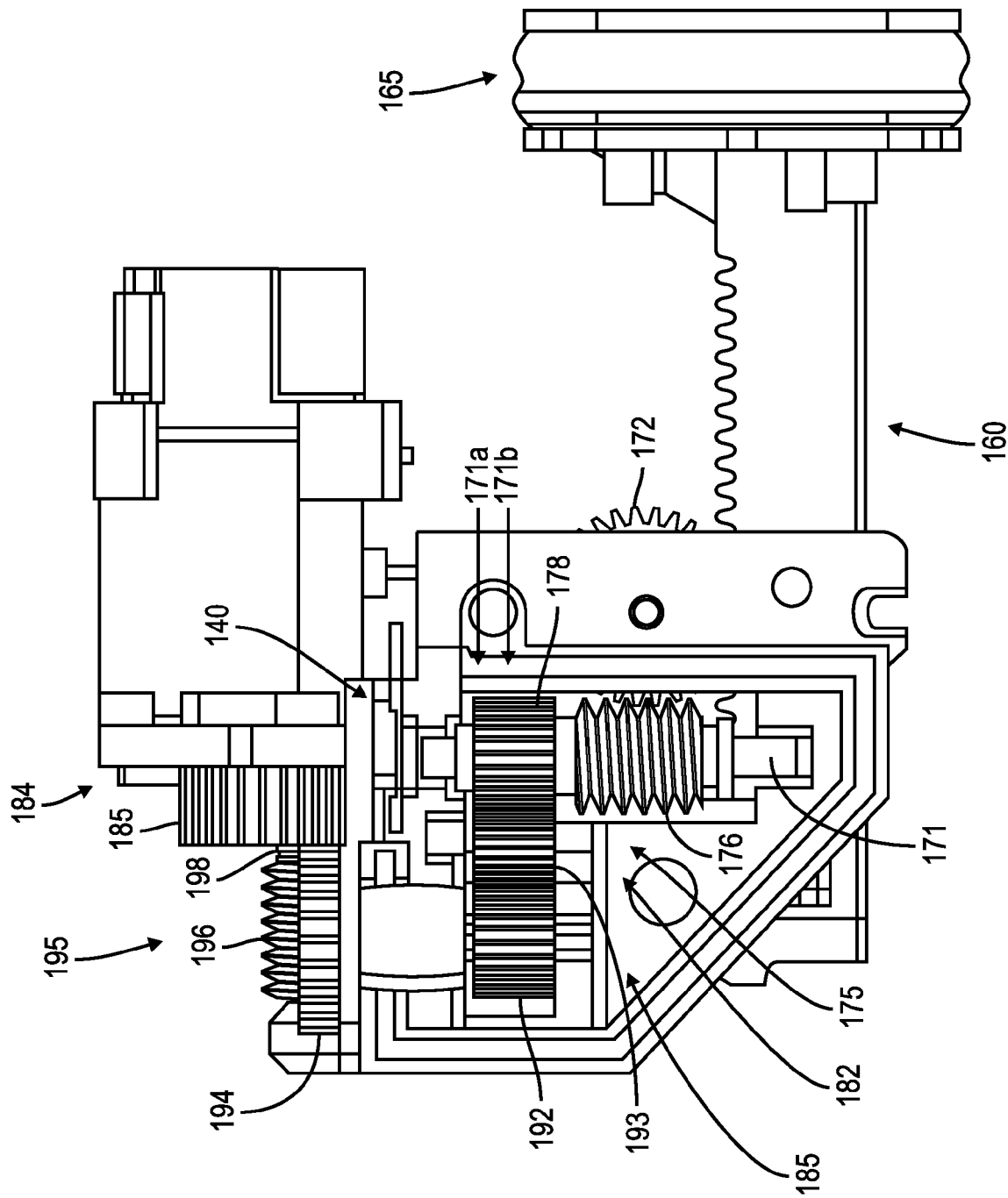
FIG. 12 illustrates a portion of a medical device system in accordance with an embodiment of the present invention.
Figure 13:
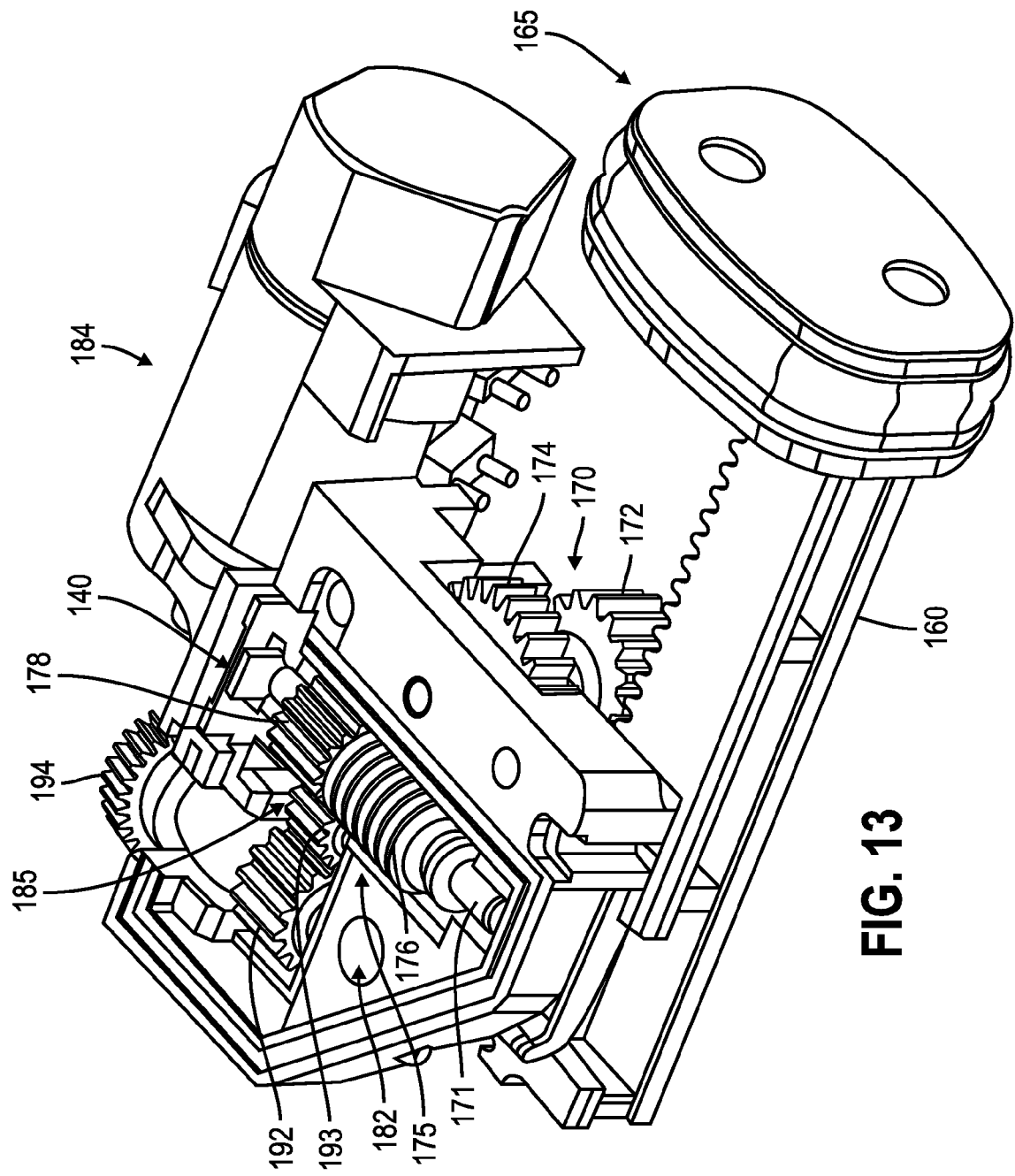
FIG. 13 illustrates a portion of a medical device system in accordance with an embodiment of the present invention.
Figure 14:
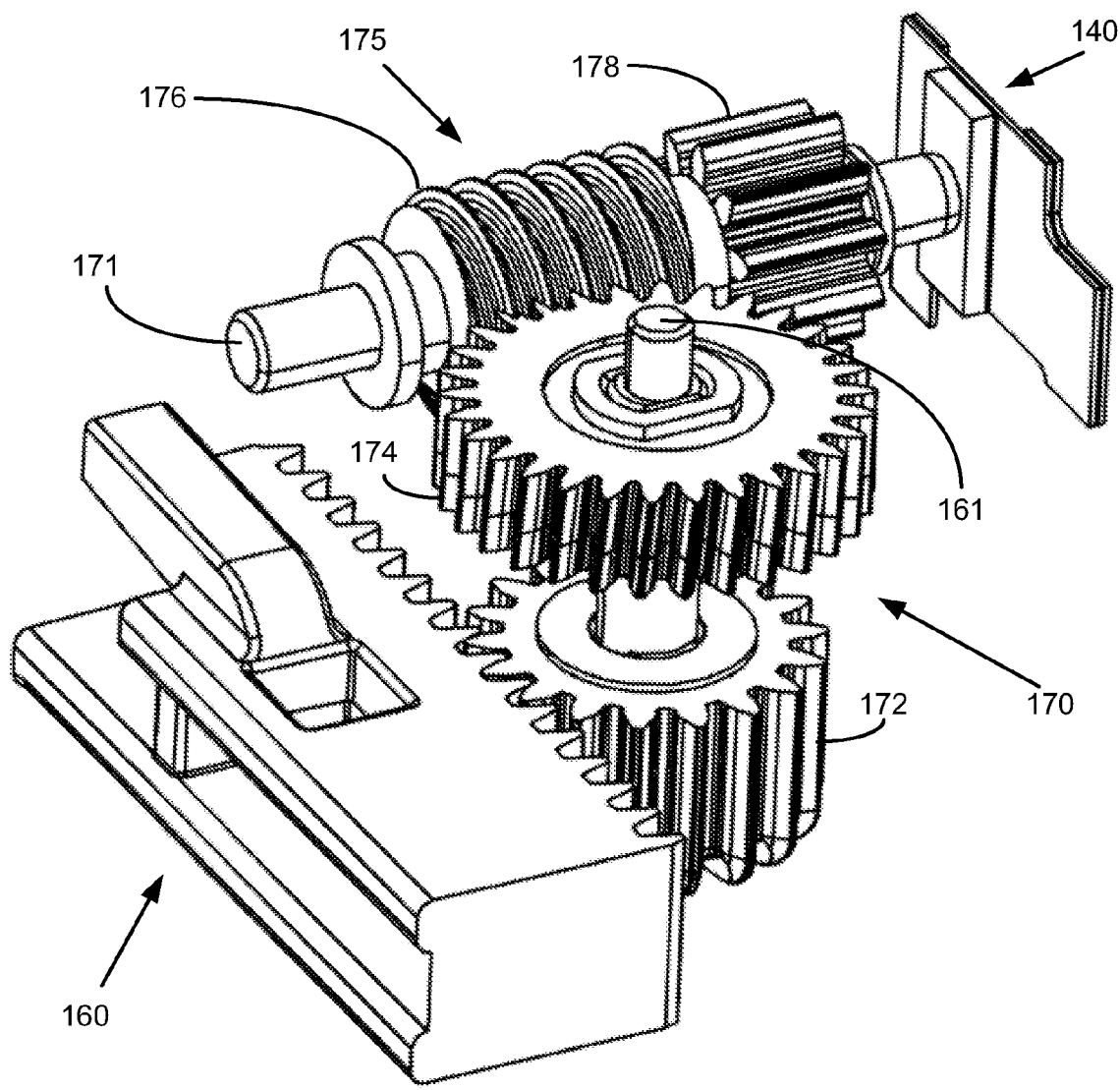
FIG. 14 illustrates a portion of a medical device system in accordance with an embodiment of the present invention.
Figure 15:
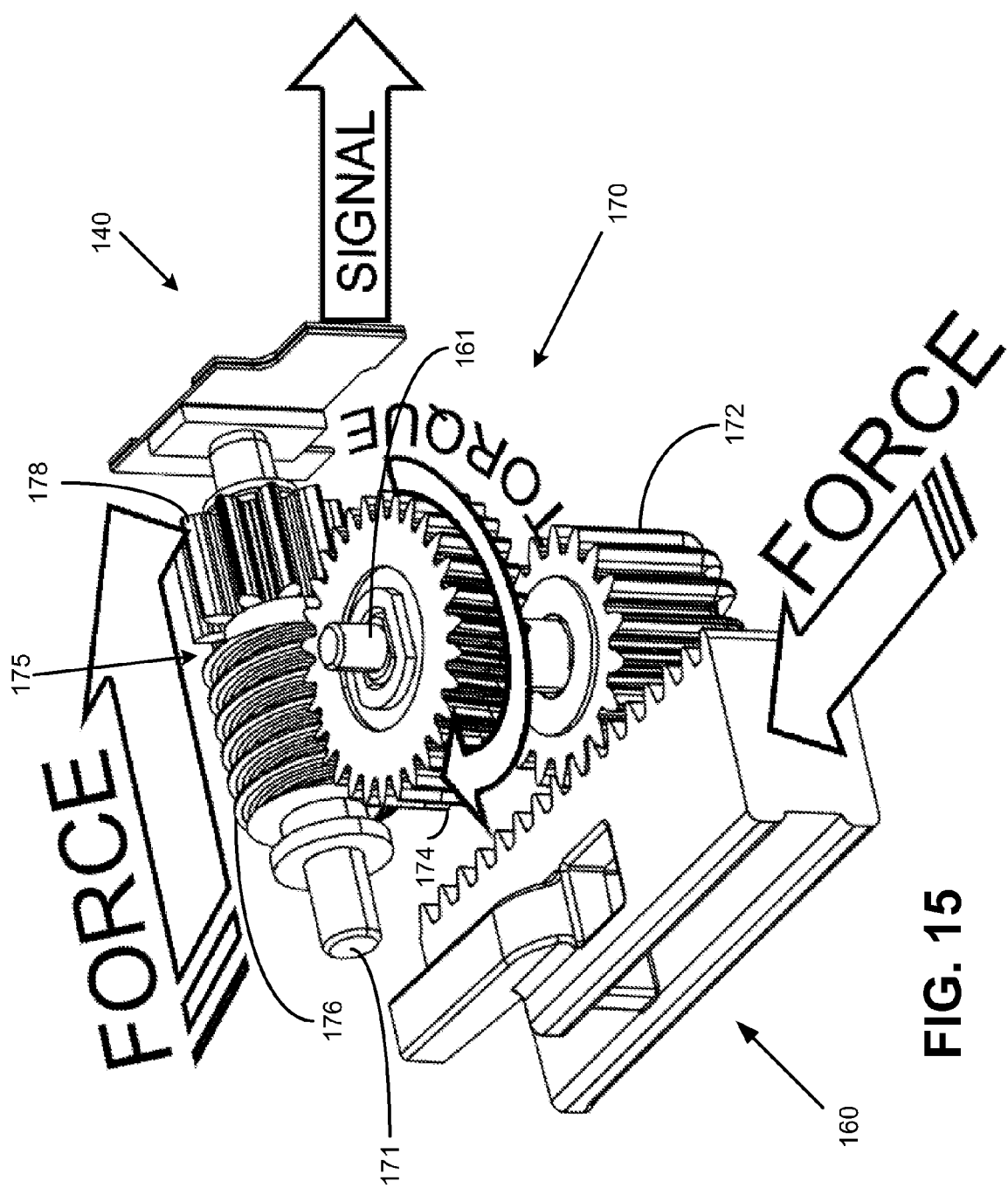
FIG. 15 illustrates a portion of a medical device system in accordance with an embodiment of the present invention.

In some embodiments, the first worm gear 174 may be supported on a shaft 161 (e.g., FIG. 8). The shaft 161 may be made of any suitable material, such as, but not limited to, plastic, metal, composite materials, and/or the like. A gear 172 (e.g., pinion gear or other suitable gear) may be supported on the shaft 161. The shaft 161 may be rotatable about an axis of the shaft 161 such that rotation of the first worm gear 174 may rotate the shaft 161 to rotate the gear 172.

In various embodiments, the gear 172 and the first worm gear 174 may be integral to each other or separate from each other. The gear 172 may be made of any suitable material, such as, but not limited to, plastic, metal, composite materials, and/or the like.

In some embodiments, the first worm gear 174 and the gear 172 may be arranged to be at least partially rotatable relative to the axis of the shaft 161 when engaging the plunger arm 160. In other words, the first worm gear 174 and the gear 172 may provide slack to allow the gear 172 to engage (e.g., mesh with) the plunger arm 160. In further or alternative embodiments, the first engagement gear 178 and the first worm 176 may be slidable along the first shaft 171 to provide slack for the first worm gear 174 and the gear 172 to engage the plunger arm 160. For instance, allowing the first engagement gear 178 and the first worm 176 to be slidable along the first shaft 171 may provide the worm gear 174 and the gear 172 sufficient freedom of movement to allow the gear 172 to rotate or otherwise move to properly align threads or teeth on the gear 172 with corresponding threads or teeth on the plunger arm 160, for example, in a manner that be may be similar that previously described.

In some embodiments, the gear 172, alone or together with the first worm gear 174, may be at least partially rotatable relative to the axis of the shaft 161 at least between a first orientation and a second orientation. In the first orientation, the gear 172 may be engageable with the plunger arm 160 when the drive device linkage portion 182 is brought together with the plunger arm 160; in the second orientation, the gear 172 may not be engageable with the plunger arm 160 when the drive device linkage portion 182 is brought together with the plunger arm 160. In some embodiments, in a case where the gear 172 is in the second orientation (i.e., the gear 172 is not engageable with the plunger arm 160), the gear 172 may be moved to the first orientation by the motor 184 (e.g., via the drive device linkage portion 182) to allow the gear 172 to engage the plunger arm 160. In further embodiments, the gear 172 may be driven by the motor 184 to remove any additional slack, for example, after the plunger arm 160 is engaged with the gear 172.

As discussed, in some embodiments, in a case where the gear 172 is in the second orientation and the drive device linkage portion 182 is brought together with the gear 172, the gear 172 may not initially engage the plunger arm 160. In further embodiments, continued relative movement of the gear 172 with the plunger arm 160 may cause the gear 172 to rotate slightly or otherwise move to the first orientation and engage the plunger arm 160 to allow the motor 184 to drive the plunger arm 160. In yet further embodiments, the gear 172 may be driven by the motor 184 to remove any additional slack, for example, after the plunger arm 160 is engaged with the gear 172.

Thus in various embodiments, the gear 172 and/or the first worm gear 174 may be configured to reduce slack between the drive device linkage portion 182 and the plunger arm 160. In further embodiments, the first worm 176 and the first engagement gear 174 may be at least partially movable (e.g., slidable) along the axis of the shaft 171 to allow the first worm gear 174 to be at least partially rotatable relative to the axis of the shaft 161. Accordingly, the gear 172 may be at least partially rotatable at least between the first orientation and the second orientation to allow the gear 172 to engage the plunger arm 160. In other embodiments, the gear 172 may be omitted with the first worm gear 174 engaged with the plunger arm 160. In such embodiments, the first worm gear 174 may be configured in a manner similar to, but is not limited to, that described throughout the disclosure with respect to the gear 172.

In some embodiments, the plunger arm 160 may be configured to include a threaded or toothed rack or the like. In such embodiments, the gear 172 may be a pinion gear or other suitable gear for engaging and moving the rack. In other embodiments, the plunger arm 160 may be configured for use with a drive screw associated with the drive device linkage portion 182, for example, the worm gear 174 or the gear 172. For instance, in such embodiments, the plunger arm 160 may be keyed to engage the drive device linkage portion 182 to allow the drive device linkage portion 182 to move the plunger arm 160. Various examples of configurations for engaging a plunger arm (or portion thereof) connected to a plunger head with a drive device linkage portion is described in, but not limited to, U.S. App. Pub. No. US 2006/0264889, filed Aug. 23, 2005, entitled "Infusion Device and Method with Drive Device in Infusion Device and Method with Drive Device in Separable Durable Housing Portion," herein incorporated by reference in its entirety.

In further embodiments, the drive device linkage portion 182 may include a second linkage portion 190. In such embodiments, the first linkage portion 170 may be operatively engaged with the second linkage portion 190 to allow the motor 184 to drive the first linkage portion 170 via the second linkage portion 190. In various embodiments, the second linkage portion 190 may be or may include one or more suitable gears, belts, chains, drive shafts or other linkage structure.

In various embodiments, the second linkage portion 190 may be configured like or include features similar to the first linkage portion 190. For instance, in some embodiments, the second linkage portion 190 may include a worm drive or other arrangement configured to allow higher torque to be transmitted between gears and/or to reduce rotational speed, which may be similar to the first linkage portion 170. In such embodiments, the second linkage portion 190 may include a second worm gear (or worm wheel) 194 arranged to engage with a complementing gear, such as a second worm 196, or the like. In particular embodiments, the second worm 196 may be supported and/or rotatable about an axis perpendicular to an axis supporting the second worm gear 194.

The second worm 196 may be operatively engaged or otherwise connected with a second engagement gear 198 (e.g., pinion gear, spur gear, and/or the like) such that the second engagement gear 198 and the second worm 196 have a shared axis of rotation. Thus, the second engagement gear 198 may be supported and/or rotatable about an axis perpendicular to an axis supporting the second worm gear 194. The second engagement gear 198 may be made of any suitable material, such as, but not limited to, plastic, metal, composite materials, and/or the like.

The second gear 198 and the second worm 196 may be supported on a second shaft 191 (e.g., FIG. 8) to allow rotational movement of the second gear 198 and the second worm 196 about the second shaft 191. The second gear 198 may be arranged to operatively engage with the motor gear 185 to allow the motor 184 to drive the second linkage portion 190. The second worm gear 194 may be arranged to operatively engage the first linkage portion 170 to allow the motor 184 to drive the first linkage portion 170. In some embodiments, the second worm 196 and the second gear 198 may be integral with each other to form a second body 195.

In some embodiments, an intermediary linkage portion 185 may be arranged between the second linkage portion 190 and the first linkage portion 170 to allow the motor 184 to convey a drive force from the second linkage portion 190 to the first linkage portion 170. In various embodiments, the intermediary drive portion 185 may be or may include one or more suitable gears, belts, chains, drive shafts or other linkage structure. For example, the intermediary drive portion 185 may include a first intermediary gear 192 and a second intermediary gear 193 that may be operatively engaged with the second worm gear 194 and the first engagement gear 178, respectively. One or both of the first intermediary gear 192 and the second intermediary gear 193 may be made of any suitable material, such as, but not limited to, plastic, metal, composite materials, and/or the like. Thus, in some embodiments, the motor gear 185, the second gear 198, the second worm 196, the second worm gear 194, the first intermediary gear 192, the second intermediary gear 194, the first engagement gear 178, the first worm 176, the first worm gear 174, and the gear 172 may form a gear train for transferring a drive force from the motor 184 to the plunger arm 160.

With reference to FIGS. 7, 8, and 12-16, in some embodiments, the drive device system 180 may further include a sensor 140 configured to sense or otherwise measure a force or torque on the plunger arm 160. For example, the force on the plunger arm 160 may be a force (e.g., linear force) in a direction opposite from a direction in which the plunger arm 160 moves in the reservoir 168 to deliver fluidic media from the reservoir 168. The force on the plunger arm 160 may be caused, for example, by an occlusion in the reservoir 168 or other condition preventing the plunger arm 160 and/or the plunger head 165 from substantially moving within or along the reservoir 168.

The force on the plunger arm 160 may correspond to torque on the first worm gear 174 and/or the gear 172. The torque on the first worm gear 174 and the gear 172 may correspond to force, such as a linear force, on the first worm 176 and the first engagement gear 178. The force on the first worm 176 and the first engagement gear 178 may be measured or otherwise sensed by the sensor 140 to measure or otherwise sense the force on the plunger arm 160. For instance, the first engagement gear 178 may contact the sensor 140 or a portion of the drive device system 180 supporting the sensor 140 to allow the sensor 140 to measure or otherwise sense the force of the first worm 176 and the first engagement gear 178. For example, the first worm gear 174 may apply a pressure to the sensor 140 or a portion of the drive device system 180 supporting the sensor 140 as the first worm gear 174 is moved to the second position. Thus, in various embodiments, a load on the plunger arm 160 may be transferred to the sensor 140 to allow the sensor 140 to measure force and/or torque on the plunger arm 160 and/or the gear 172 and the first worm gear 174, respectively.

For example, the plunger arm 160 may be advanced in a first direction within the reservoir 168 to deliver fluidic media. In a case where the plunger arm 160 is substantially prevented from advancing within the reservoir 168 (e.g., an occlusion in the reservoir 168), a force on the plunger arm 160 may move the plunger arm 160 and/or the gear 172 engaged with the plunger arm 160 in a second direction, opposite the first direction in which the plunger arm 160 advances to deliver fluidic media. As a result, the worm 176 and the engagement gear 178 may be moved toward or against the sensor 160 (e.g., toward the second position 171b). Accordingly, the sensor 160 may measure the force applied by the worm 176 and the engagement gear 178 to measure the force on the plunger arm 160.

In some embodiments, circuitry 420 that includes a processor 422 associated with the sensor 140, for example via bus 421, may be configured to execute various programs or algorithms and/or to process various information, such as data received from the sensor 140. The processor 422, for example, may be configured to compare detected signals with threshold values and/or pre-stored values in memory 424.

For instance, in some embodiments, the processor 422 may be configured to carry out certain processing in a case where the sensor 140 measures a force, for example, indicating that an occlusion is present. For example, the processor 422 may provide a signal to the motor 184 to stop the motor 184 from driving the plunger arm 160, drive device linkage portion 182, and/or the like. As another example, the processor 422 may provide a signal to an indicator device to alert a user-patient of the occlusion. Examples of indicator devices may be similar to, but are not limited to, those described in U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

In some embodiments, the drive device linkage portion 182 may be driven by the motor 184, which may be controlled by the processor 422, to substantially remove any slack in the drive device linkage portion 182 and/or the plunger arm 160, for example, after the plunger arm 160 is engaged with the gear 172 to prime the drive device system 180. For instance, a drive device system 180 having little or no slack may correspond to a first profile (e.g., a first torque profile), and a drive device system 180 with slack, for example after the plunger arm 160 engages with the gear 172, may correspond to a second profile (e.g., a second torque profile). That is, a range of rotational motion of one or more gears relative to, for example, the plunger arm 160 meeting a threshold value or within a range may correspond to a first profile, and a range of rotational motion of one or more gears relative to, for example, the plunger arm 160 exceeding/below a threshold value or outside a range may correspond to the second profile.

Thus, in case where slack is present and/or the sensor 140 senses the second profile, the motor 184 may drive the drive device linkage portion 182 until the sensor 140 senses the first profile (and/or associated circuitry, such as the processor 422, determines that the first profile has been reached) indicating that the slack has been substantially removed. Accordingly, in various embodiments, the drive device system 180 has been primed. Torque profiles may refer to, but are not limited to, an expected torque value (e.g., for a given position of the worm body 175), torque as a measurement of a second parameter (e.g., time, position, and/or the like), and/or the like.

As a non-liming example, in a case where an acceptable threshold value is five degrees or less in a clockwise and counterclockwise direction, a drive device system 180 having a gear that a range of rotational motion of twenty degrees in a clockwise and counterclockwise direction may correspond to the second profile. Accordingly, the motor 184 may drive the drive device linkage portion 182 to reduce the range of rotational motion of the gear to five degrees or less, which corresponds to the second profile. Once the second profile is met, for example as sensed by the sensor 140, the motor 184 may stop driving the drive device linkage portion 182.

As another example, the motor 184 may drive the drive device linkage portion 182 until a measurement of the force (or torque) by the sensor 140 meets a certain threshold range (and/or associated circuitry, such as the processor 422, determines that the measurement has met the certain threshold). A measurement meeting the certain threshold range may indicate that the slack has been substantially removed or is otherwise not present. Accordingly, various embodiments may allow for priming of a drive device system based on algorithms employing measurements from a force sensor. In further embodiments, the processor 422 may be configured to provide a signal to control circuitry to allow operation of the delivery device 12 (e.g., FIGS. 1-6C) in a case where the first profile is sensed by the sensor 140 (and/or associated circuitry, such as the processor 422) determines that the first profile has been reached or is otherwise present.

Thus in various embodiments, a sensor may be provided and/or configured to sense a force on a plunger arm and/or to prime a delivery device to substantially reduce slack after a plunger arm is engaged with a drive device linkage portion.

As discussed, the processor 422 may be associated with the sensor 140, for example via the bus 421. The processor 422 may be configured to execute various programs or algorithms and/or to process various information, such as data received from the sensor 140. The processor 422, for example, may be configured to compare detected signals with threshold values and/or pre-stored values in the memory 424.

In some embodiments, the force sensed or otherwise measured by the sensor 140 may be a parameter for use in an algorithm, for example, for calculating force or torque on the plunger arm 160 (and/or other associated components, such as the plunger head 165, and/or the like) and/or other information derivable from the force sensed or otherwise measured by the sensor 140. In particular embodiments, the parameter may be used in an algorithm for detecting an occlusion in the reservoir 168, or the like. The occlusion may be caused, for example, by a blockage in the reservoir 168. In such a case, the occlusion may result in increased pressure within the reservoir 168. In various embodiments, the algorithm may be carried by, but is not limited to, the processor 422.

With reference to FIGS. 7-17, in some embodiments, one or more algorithms may be employed using one or more parameter(s) relating to a position of the plunger head 165 (or the plunger arm 160) relative to a first position (e.g., a starting position). For instance, the one or more parameter(s) may be compared with predetermined threshold values and/or ranges. Accordingly, depending on how some (or all) of the one or more parameter(s) compare with the predetermined threshold values and/or ranges (e.g., the parameter(s) match the threshold value(s) or a difference between the parameter(s) and the threshold value(s) exists), the position of the plunger head 165 (or the plunger arm 160) may be determined by the processor 422 via the one or more algorithms.

The parameter(s) may be determined based on signals or signal parameters relating to, but not limited to, any one of or combination of: (i) an amount the motor 184 (or other drive device) or portion associated with the motor 184 (e.g., motor gear 185) controlled (e.g., programmed) to move; (ii) an amount the motor 184 (or other drive device) or portion associated with the motor 184 is moved; and (iii) an amount the plunger head 165 (and/or the plunger arm 160) actually moved. In particular embodiments, the parameter(s) relating to the position of the plunger head 165 may correspond to a volume of fluidic media in the reservoir 168, for example, a volume of fluidic media remaining in and/or delivered from the reservoir 168. Thus, in various embodiments a volume in a reservoir may be measurable with an algorithm employing any one of or combination of signals or signal parameters relating to a drive device, plunger arm, and/or plunger head.

In various embodiments, the parameter(s) employed by the one or more algorithms (or other algorithm(s)) may be determined based on, in addition to or alternatively from, some or all of the signals or signal parameters previously described, signals or signal parameters that may include, but are not limited to, any one of or combination of: energy used by the motor (or other drive device), motor current, voltage to motor, comparison with known parameter(s) of a delivery of a known amount of fluidic media (e.g., voltage required for a delivery of a known amount of fluidic media), back electromagnetic force (BEMF), and/or the like. In other embodiments, such signals or signal parameters may provide one or more parameters that are distinct from the parameter(s) previously described.

In various embodiments, the parameter(s) employed by the one or more algorithms (or other algorithm(s)) may be determined based on, in addition to or alternatively from some or all of the signals or signal parameters previously described, signals or signal parameters that may be provided by one or more sensors, such as, but not limited to, any one of or combination of: from an occlusion sensor, from the sensor 140 (e.g., measuring or otherwise sensing force and/or torque on the plunger arm 160 and/or drive device linkage portion 182), and/or the like. Examples of signals or signal parameters from various sensors employable in one or more algorithms employable by the processor 422 may be similar to those disclosed in, but are not limited to, U.S. Pat. Pub. No. US 2006/0184154, filed Dec. 30, 2005, entitled "Methods and Apparatuses for Detecting Occlusions in an Ambulatory Infusion Pump"; and U.S. Pat. Pub. No. US 2007/0191770, filed Nov. 20, 2006, entitled "Method and Apparatus for Detecting Occlusions in an Ambulatory Infusion Pump," all of which are herein incorporated by reference in their entirety. In other embodiments, such signals or signal parameters may provide one or more parameters that are distinct from the parameter(s) previously described.

As discussed, in some embodiments, one or more parameter(s) relating to a position of a plunger head 165 may be based, at least partially, on signals or signal parameters relating to an amount a motor 184 (or other drive device) or portion associated with the motor 184 is controlled to move, for example, by control circuitry, such as, but not limited to, the circuitry 420, the processor 422, and/or the like. For instance, a number of revolutions a gear, such as the gear 185, or shaft (e.g., shaft 181) supporting the gear is controlled to rotate may correspond to the amount. In further embodiments, a control signal, for example from the control circuitry of the motor 184 may be used to determine the amount the gear or shaft rotates. In such embodiments, the motor 184 may be, but is not limited to, a step motor, or the like. In other embodiments, other suitable motors controlled by a signal, such as, but not limited to, a DC motor, voice coil motor, three-phase motor, and/or the like, may be employed. In some embodiments, such a parameter instead may be related to a position of the plunger arm 160 (or portion thereof) connected to the plunger head 165.

As discussed, in some embodiments, one or more parameter(s) relating to a position of a plunger head 165 may be based, at least partially, on signals or signal parameters relating to an amount a motor 184 (or other drive device) or portion associated with the motor 184 actually moved. For instance, a number of revolutions a gear (e.g., motor gear 185) or shaft (e.g., shaft 181) supporting the gear is rotated may correspond to the amount.

In further embodiments, a rotary encoder (e.g., optical, magnetic, and/or the like) and sensor (not shown) for sensing the rotary encoder may be provided. The rotary encoder and/or the sensor may be associated with the motor 184 to determine the amount moved by the motor 184 or the portion associated with the motor 184. For instance, in some embodiments, the rotary encoder may be provided on the gear (e.g., motor gear 185) or the shaft (e.g., shaft 181) and the sensor for sensing the rotary encoder provided at a suitable location, such as on or near the motor 184. In various embodiments, the sensor and the rotary encoder may be used to measure a number of revolutions of the motor gear 185, shaft 181, and/or the like. Accordingly, the number of revolutions by the motor gear 185, as measured by the sensor and the encoder, may correspond to the amount the motor 184 or the portion associated with the motor 184 actually moved.

As discussed, in particular embodiments, the sensor may be on the motor 184. In other embodiments, the sensor may be arranged along any suitable position to interact with the rotary encoder. In particular embodiments, the sensor (or other sensor, such as an occlusion sensor) may be on a same portion (e.g., on a circuit board) to which the motor 184 and/or the encoder is attached. Such embodiments may allow for reduction in cost, increased reliability of signals (e.g., fewer connections), availability of amplification, and/or the like.

As discussed, in some embodiments, one or more parameter(s) relating to a position of a plunger head 165 (or a plunger arm 160) may be based, at least partially, on signals or signal parameters relating an amount a plunger head 165 moved, for example, from a known position. In further embodiments, a volume sensor (not shown) associated with the reservoir 168 may be used to determine the position of the plunger head 165. For example, a volume sensor may be provided on the plunger head 165 (or the plunger arm 160). Examples of volume sensors and other sensors are disclosed in, but are not limited to, U.S. patent application Ser. No. 12/649,619, filed Dec. 30, 2009, entitled "Alignment Systems and Methods," herein incorporated by reference in its entirety. For example, the volume sensor may provide data that the plunger head 165 (and/or the plunger arm 160) has moved several centimeters.

Figure 18:
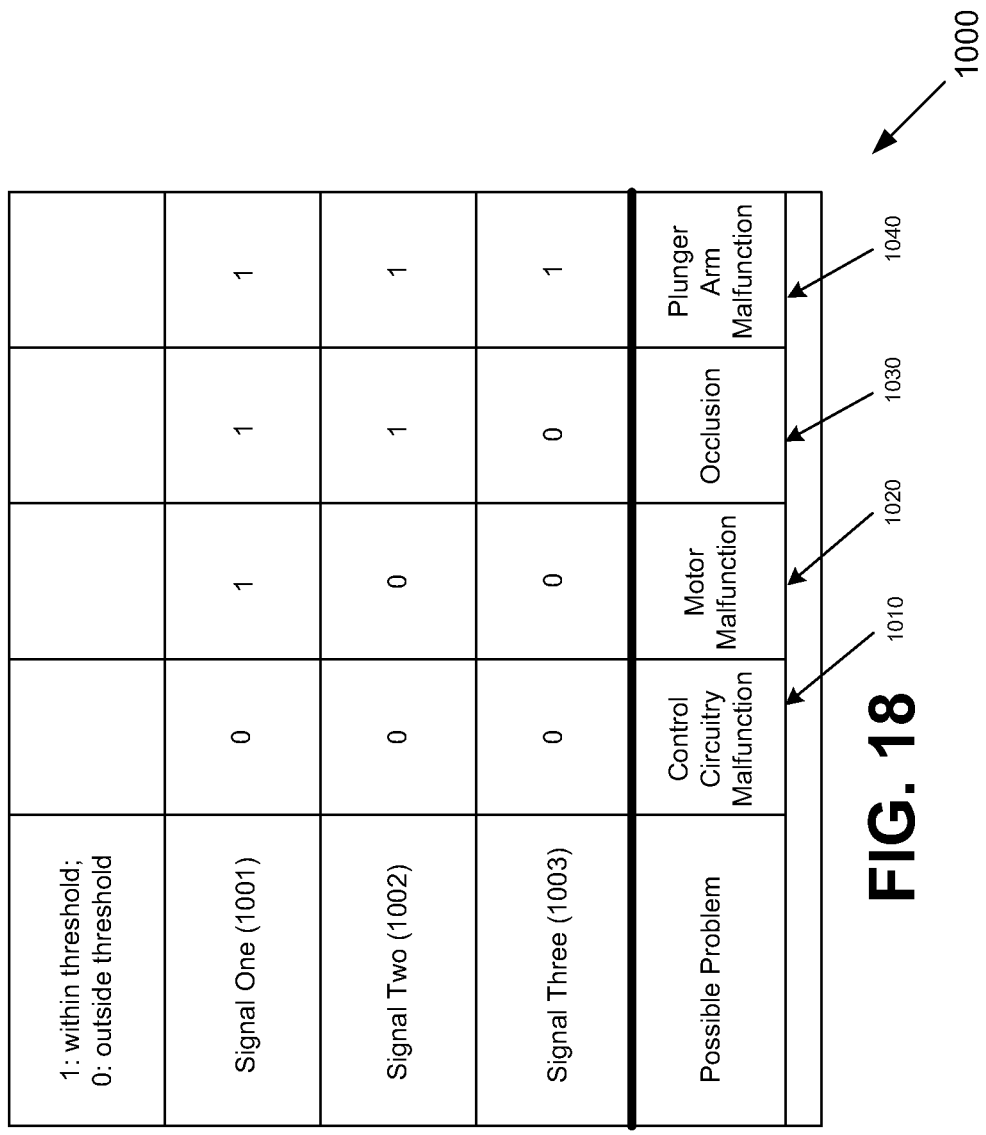
FIG. 18 illustrates an exemplary matrix in accordance with an embodiment of the present invention.

In various embodiments, one or more algorithm(s) may be used by the processor 422 that employs one or more of the three signals or signal parameters above, in addition to or in alternative of, but not limited to, any of the other listed signals or signal parameters to detect a volume within the reservoir 168. For instance, each of the signals or signal parameters used by the algorithm may be checked by the processor 422 to determine whether each of the signals or signal parameters meets a predetermined value or is within a specified range, for example, to allow for an acceptable tolerance. Accordingly, the algorithm(s) may be used by the processor 422 to determine proper operating conditions of the delivery device. In various embodiments, one or more algorithm(s) may be used by the processor 422 that employs one or more of the three signals or signal parameters above, in addition to or in alternative of, but not limited to, any of the other listed signals or signal parameters to detect a condition of the delivery device. FIG. 18 is an non-limiting example of a matrix 1000 illustrating possible operating conditions and/or malfunctions that may be identified or otherwise determined by the processor 422 based on one or more signals or signal parameters, such as, but not limited to, those previously described. With respect to FIG. 18, a "1" may indicate a particular signal or signal parameter meets a predetermined value or is within a specified threshold. A "0" may indicate a particular signal or signal parameter does not meet a predetermined value or is not within a specified threshold.

In some embodiments, the processor 422 (or the circuitry 420) may be configured to carry out certain processing based on the operating conditions (and/or malfunctions) determined by the processor 422. For example, the processor 422 may provide a signal to the motor 184 to stop the motor 184 from driving the plunger arm 160 any further. As another example, the processor 422 may provide a signal to or change a state of an indicator device 425, such as display device, or the like, to alert the user-patient of the occlusion. Examples of indicator devices may be found in, but are not limited to, U.S. patent application Ser. No. 11/759,725, entitled "Infusion Medium Delivery Device and Method with Drive Device for Driving Plunger in Reservoir"; and U.S. patent application Ser. No. 12/649,619, filed Dec. 30, 2009, entitled "Alignment Systems and Methods," both of which are herein incorporated by reference in their entirety.

With reference to FIGS. 7-18, according to a non-limiting exemplary embodiment, in a case where signal one 1001 (e.g., corresponding to an amount the motor 184 controlled to move), signal two 1002 (e.g., corresponding to an amount the motor 184 moved), and signal three 1003 (e.g., corresponding to an amount the plunger head 165 moved) are each outside their respective specified range (or otherwise do not meet their respective predetermined value), the processor 422 may identify or otherwise determine a first operating condition 1010. The first operating condition 1010 may indicate that one or more problem(s) has/have occurred. For instance, such a condition may result if the motor 184 is not controlled to move (an expected amount, if at all), the motor 184 is not moved (an expected amount, if at all), and the plunger head 165 is not moved (an expected amount, if at all). Accordingly, the processor 422, for example, may determine that a malfunction with the control circuitry, as described, for example, with respect to FIGS. 1-6C, has occurred.

Returning to FIGS. 7-18, in a case where the signal one 1001 is within its specified range (or otherwise meets its predetermined value), and the signal two 1002 and the signal three 1003 are each outside their respective specified range (or otherwise do not meet their respective predetermined value), the processor 422 may identify or otherwise determine a second operating condition 1020. The second operating condition 1020 may indicate that one or more problem(s) has/have occurred. For instance, such a condition may result if the motor 184 is not moved (an expected amount, if at all) and the plunger head 165 is not moved (an expected amount, if at all). Accordingly, the processor 422 may determine, for example, that a malfunction with the motor 184 has occurred.

In a case where the signal one 1001 and the signal two 1002 are each within their respective specified range (or otherwise meet their respective predetermined values), and the signal three 1003 is outside its respective specified range (or otherwise does not meet its predetermined value), the processor 422 may identify or otherwise determine a third operating condition 1030. The third operating condition 1030 may indicate that one or more problems have occurred. For instance, such a condition may result if the plunger head 165 is not moved (an expected amount, if at all). Accordingly, the processor 422 may determine, for example, that an occlusion has occurred in the reservoir 168.

In a case where the signal one 1001, the signal two 1002, and the signal three 1003 are each within their respective specified range (or otherwise meet their respective predetermined values), the processor 422 may identify or otherwise determine a fourth operating condition 1040. In some embodiments, the fourth operating condition 1040 may indicate that the delivery device (or portion thereof) is operating properly. In other embodiments, the fourth operating condition 1040 may indicate that some other possible condition, such as one or more problems, has occurred, such as, for example, a malfunction with the plunger arm. For instance, such a condition may result if the motor 184 is controlled to move an expected amount, the motor 184 is moved an expected amount, and the plunger head 165 is moved an expected amount. Accordingly, the processor 422 may determine, for example, that a malfunction with the plunger arm 160 has occurred.

In some embodiments, a malfunction may be listed as a possible condition for more than one occurrence (e.g., more than one combination of signals or signal parameters). For example, in a case where the signal one 1001, the signal two 1002, and the signal three 1003 are each outside their respective specified range (or otherwise do not meet their respective predetermined value), the processor 422 may determine that a control circuitry malfunction (e.g., 1010), motor malfunction (e.g., 1020), occlusion (e.g., 1030), and/or a plunger malfunction (e.g., 1040) has occurred.

As discussed, other matrixes may include a fewer or greater number of signals or signal parameters, that for example include, but are not limited to, any of the other listed signals or signal parameter, in addition to or in alternative of the three signals or signal parameter previously discussed. For instance, a signal or signal parameter from an occlusion sensor may be employed in the algorithm. For example, in a case where an occlusion sensor detects that force is increasing within a reservoir 168 and an amount a plunger head 165 moves does not change, the processor 422 may determine, for example, that an occlusion is occurring.

In some embodiments, the algorithm(s) employed by the processor 422 may use a value corresponding to each (or some) of the signals or parameter signals. In such embodiments, a first value outside a specified range may have an associated result different from an associated result of a second value outside the specified range. For example, with reference to FIG. 20, the signal three 1003 may have a specified range of 2 to 4 (i.e., the signal three 1003 may be determined to be acceptable in a case where the signal three 1003 has a value of 2 to 4). In such an example, in a case where the signal one 1001 and the signal two 1002 are each within their respective specified range (or otherwise meet their respective predetermined value), and the signal three 1003 has a value of 0, the processor 422 may determine, for example, an occlusion is occurring. In a case where the signal one 1001 and the signal two 1002 are each within their respective specified range (or otherwise meet their respective predetermined value), and the signal three 1003 has a value of 1, the processor 422 may determine, for example, there is a malfunction with the plunger arm 160.

In a case where the signal one 1001 and the signal two 1002 are each within their respective specified range (or otherwise meet their respective predetermined value), and the signal three 1003 has a value of 2 (or 3 or 4) (i.e., the signal three 1003 is within its specified range), the processor 422 may determine that the delivery device is operating properly. In a case where the signal one 1001 and the signal two 1002 are each with their respective specified range (or otherwise meet their respective predetermined value), and the signal three 1003 has a value of 5 (or higher), the processor 422 may determine, for example, there has been a malfunction with the plunger head 165.

With reference to FIGS. 7-18, in some embodiments, one or more of the algorithms described may be used to error check or otherwise calibrate an occlusion sensor. Various examples of occlusion sensors are disclosed in, but are not limited to, U.S. Pat. No. 6,485,465, filed Mar. 27, 2001, entitled "Methods, Apparatuses, and Uses for Infusion Pump Fluid Pressure and Force Detection"; U.S. Pat. Pub. No. US 2006/0184154, filed Dec. 30, 2005, entitled "Methods and Apparatuses for Detecting Occlusions in an Ambulatory Infusion Pump"; and U.S. Pat. Pub. No. US 2007/0191770, filed Nov. 20, 2006, entitled "Method and Apparatus for Detecting Occlusions in an Ambulatory Infusion Pump," all of which are herein incorporated by reference in their entirety.

In some embodiments, measurements from the sensor 140 may be used to control or otherwise calibrate the motor 184. For instance, the motor 184 may be controlled to move, for example, by the processor 422 or other circuitry until the sensor 140 measures a desired result, for example a reduced amount of slack, which may correspond to a first torque profile.

In various embodiments, one or more algorithm(s), which may include, but is not limited to, one or more of the algorithms described, may be used by the processor 422 that employs one or more of the three signals above, in addition to or in alternative of, but not limited to, any of the other listed signals to provide feedback to or otherwise calibrate the sensor 140.

In further embodiments, the sensor 140 may be calibrated based on measurements taking from various sensors of the delivery device, such as an occlusion sensor, a reservoir volume sensor, and/or the like. Various examples of occlusion sensors and other sensors are disclosed in, but are not limited to, U.S. Pat. No. 6,485,465, filed Mar. 27, 2001, entitled "Methods, Apparatuses, and Uses for Infusion Pump Fluid Pressure and Force Detection"; U.S. Pat. Pub. No. US 2006/0184154, filed Dec. 30, 2005, entitled "Methods and Apparatuses for Detecting Occlusions in an Ambulatory Infusion Pump"; and U.S. Pat. Pub. No. US 2007/0191770, filed Nov. 20, 2006, entitled "Method and Apparatus for Detecting Occlusions in an Ambulatory Infusion Pump," all of which are herein incorporated by reference in their entirety. Various examples of volume sensors and other sensors are disclosed in, but are not limited to, U.S. patent application Ser. No. 12/649,619, filed Dec. 30, 2009, entitled "Alignment Systems and Methods," herein incorporated by reference in its entirety.

For instance, a measurement from a volume sensor (not shown) and the sensor 140 may be employed in a suitable algorithm to calculate an output shift (e.g., signal drift) of the sensor 140 caused, for example, by environmental conditions, such as, but not limited to, temperature, humidity, pressure, and/or the like. For example, a measurement from the volume sensor can be compared to a measurement of the sensor 140. As such, a difference between the measurement of the sensor 140 and an expected measurement of the sensor 140 corresponding to the measurement from the volume sensor can be adjusted or otherwise compensated. Accordingly, the output shift of the sensor 140 may be corrected based on, for example, the measurement of the volume sensor.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A delivery device for delivering fluidic media, the delivery device comprising:
 a first housing portion adapted to be secured to a user;
 a second housing portion configured to be selectively engaged with and disengaged from the first housing portion, one of the first housing portion and the second housing portion for supporting a reservoir for containing fluidic media;
 a drive device configured to be operatively engagable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir; and
 a drive linkage for operatively engaging the drive device with the plunger arm to allow the drive device to move the plunger arm, the drive linkage including a first gear and a second gear operatively engaged with each other, the first gear engageable with the plunger arm, the second gear supported on a shaft having an axis and a longitudinal dimension, the second gear supported for rotation about the axis of the shaft, the second gear supported for lateral movement in a direction along the longitudinal dimension of the shaft such that the lateral movement of the second gear allows the first gear to engage the plunger arm.

2. The delivery device according to claim 1, the drive linkage comprising a worm and a worm gear operatively engaged with the worm, the worm gear for operatively engaging the plunger arm, the worm having an engagement gear operatively engaged with the drive device such that the worm is moveably driven with rotation of the engagement gear by the drive device.

3. The delivery device according to claim 2,
 wherein the first gear comprises the worm gear; and
 wherein the second gear comprises the worm and the engagement gear.

4. The delivery device according to claim 2, wherein the worm and the engagement gear are integral to each other.

5. The delivery device according to claim 2, wherein the worm and the engagement gear comprise plastic.

6. The delivery device according to claim 1, the second gear configured to be movable along the longitudinal dimension of the shaft at least between a first position and a second position.

7. The delivery device according to claim 6, the second gear configured to be moveable to the first position to reduce a rotational range of motion of the first gear relative to the plunger arm in a case where the first gear and the plunger arm are engaged and the second gear is in the second position.

8. The delivery device according to claim 7, wherein the second gear is configured to be moved to the first position by the drive device.

9. The delivery device according to claim 7, the delivery device further comprising:
a sensor configured to measure a pressure on the sensor caused by the second gear.

10. The delivery device according to claim 9,
wherein the pressure on the sensor caused by the second gear corresponds to a force on the plunger arm; and
wherein the second gear contacts at least one of the sensor or a structure supporting the sensor in a case where the second gear is in the first position.

11. The delivery device according to claim 6, the delivery device further comprising:
a sensor configured to measure a pressure on the sensor caused by the second gear, the pressure on the sensor caused by the second gear corresponding to a force on the plunger arm.

12. The delivery device according to claim 11,
wherein the plunger arm and the first gear are arranged so that the force on the plunger arm applies a torque on the first gear; and
wherein the first gear and the second gear are arranged so that the torque on the first gear applies a force on the second gear for applying pressure to the sensor in a case where the second gear is in the second position.

13. The delivery device of claim 6,
the shaft having a first end and a second end defining the longitudinal dimension of the shaft;
wherein the second gear is a first distance away from the first end of the shaft, in the first position; and
wherein the second gear is a second distance, different from the first distance, away from the first end of the shaft, in the second position.

14. The delivery device according to claim 1, the second gear configured to be slidable along the longitudinal dimension of the shaft.

15. The delivery device according to claim 1, wherein the first gear is supported on a rotatable shaft for rotational movement about an axis of the rotatable shaft, the first gear for operatively engaging the plunger arm to allow the drive device to drive fluidic media from the reservoir in a case where the drive device is operatively engaged with the reservoir and the plunger arm is moved in the axial direction relative to the reservoir.

16. The delivery device according to claim 15, the first gear further comprising a gear supported on the rotatable shaft for rotational movement about the axis of the rotatable shaft, the gear for engaging the plunger arm to allow the drive device to drive fluidic media from the reservoir in a case where the drive device is operatively engaged with the reservoir and the plunger arm is moved in the axial direction relative to the reservoir.

17. The delivery device according to claim 16,
the gear having one of threads and teeth, the plunger arm having one of corresponding threads and teeth for mating with the one of the threads and teeth of the gear upon the one of the threads and teeth of the gear aligning with the one of the corresponding threads and teeth of the plunger arm;
wherein the first gear and the plunger arm are arranged so that the gear engages the plunger arm in a case where the one of the threads and teeth of the gear align with the one of the corresponding threads and teeth of the plunger arm.

18. The delivery device according to claim 16, wherein the gear comprises a pinion gear.

19. The delivery device according to claim 15, wherein at least one of (i) the second gear is arranged to be at least partially slidable along the shaft to allow the first gear to rotate to an orientation for allowing the first gear to operatively engage the plunger arm and (ii) the first gear is arranged to be at least partially rotatable about the axis of the rotatable shaft to allow the first gear to rotate to an orientation for allowing the first gear to operatively engage the plunger arm.

20. The delivery device according to claim 19,
the first gear having one of threads and teeth, the plunger arm having one of corresponding threads and teeth for mating with the one of the threads and teeth of the first gear upon the one of the threads and teeth of the first gear aligning with the one of the corresponding threads and teeth of the plunger arm;
wherein the first gear and the plunger arm are arranged so that the first gear engages the plunger arm in a case where the one of the threads and teeth of the first gear align with the one of the corresponding threads and teeth of the plunger arm.

21. The delivery device according to claim 19, the first gear configured to operatively engage the plunger arm in a case where the first gear and the plunger arm are brought together and the first gear is in a first orientation relative to the plunger arm.

22. The delivery device according to claim 21, the first gear configured to be moveable to the first orientation relative to the plunger arm from a second orientation relative to the plunger arm in a case where the first gear and the plunger arm are brought together and the first gear is in the second orientation relative to the plunger arm.

23. The delivery device according to claim 22, wherein the first gear is not engageable with the plunger arm in the second orientation.

24. The delivery device according to claim 15, wherein the plunger arm comprises at least one of a drive screw and a rack having threads extending along a longitudinal dimension of the rack for operatively engaging with the first gear to allow the drive device to drive fluidic media from the reservoir in a case where the drive device is operatively engaged with the reservoir and the plunger arm is moved in the axial direction relative to the reservoir.

25. A delivery device according to claim 1, further comprising:
processing electronics configured to process a plurality of signals or signal parameters, including a first signal or signal parameter representing a first operating condition of the delivery device, a second signal or signal parameter representing a second operating condition of the delivery device, and a third signal or signal parameter representing a third operating condition of the delivery device;
the processing electronics further configured to determine whether each of the plurality of signals or signal parameters meets a respective predetermined parameter;
the processing electronics further configured to determine a result based on whether each of the plurality of signals or signal parameters met the respective predetermined parameter and to provide a signal based on the result representing the operating condition of the delivery device.

26. The delivery device of claim 25, wherein the signal comprises a user-perceptible indication to a user.

27. The delivery device of claim 25, wherein the delivery device is operating properly in a case where each of the plurality of signals or signal parameters meets the respective determined parameter.

28. The delivery device of claim 25, wherein the first signal or signal parameter corresponds to an amount a drive device is controlled to move by the circuitry.

29. The delivery device of claim 25, wherein the second signal or signal parameter corresponds to an amount the drive device is moved by the circuitry.

30. The delivery device of claim 25, wherein the third signal or signal parameter corresponds to an amount the plunger head is moved.

31. The delivery device of claim 25,
wherein the first signal or signal parameter corresponds to an amount a drive device is controlled to move by the circuitry;
wherein the second signal or signal parameter corresponds to an amount the drive device is moved by the circuitry; and
wherein the third signal or signal parameter corresponds to an amount the plunger head is moved.

32. The delivery device of claim 1,
the shaft having a first end and a second end defining the longitudinal dimension of the shaft;
the second gear configured for lateral movement between the first end and the second end of the shaft.

33. The delivery device of claim 1,
the shaft having a first end and a second end defining the longitudinal dimension of the shaft;
the second gear configured for lateral movement relative to the first end and the second end of the shaft.

34. The delivery device of claim 1, wherein the shaft extends through the second gear.

35. The delivery device of claim 1,
the shaft having a first end and a second end defining the longitudinal dimension of the shaft;
wherein the shaft is configured for lateral movement with the second gear.

36. The delivery device of claim 35,
wherein the first gear is a first distance away from the first end of the shaft, in the first position; and
wherein the first gear is a second distance away from the first end of the shaft, in the second position.

37. A method of making a delivery device for delivering fluidic media, the method comprising:
adapting a first housing portion to be secured to a user;
configuring a second housing portion to be selectively engaged with and disengaged from the first housing portion, one of the first housing portion and the second housing portion for supporting a reservoir for containing fluidic media;
configuring a drive device to be operatively engagable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir;
operatively engaging a drive linkage operatively engaged between the drive device and the plunger arm; and
providing a drive linkage for operatively engaging the drive device with the plunger arm to allow the drive device to move the plunger arm, the drive linkage including a first gear and a second gear operatively engaged with each other, the first gear engageable with the plunger arm, the second gear supported on a shaft having an axis and a longitudinal dimension, the second gear supported for rotation about the axis of the shaft, the second gear supported for lateral movement in a direction along the longitudinal dimension of the shaft such that the lateral movement of the second gear allows the first gear to engage the plunger arm.

38. A delivery device for delivering fluidic media, the delivery device comprising:
a first housing portion adapted to be secured to a user;
a second housing portion configured to be selectively engaged with and disengaged from the first housing portion, one of the first housing portion and the second housing portion for supporting a reservoir for containing fluidic media;
a drive device configured to be operatively engagable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir; and
a drive linkage for operatively engaging the drive device with the plunger arm to allow the drive device to move the plunger arm; and
a sensor configured to measure a force on the drive linkage corresponding to a force on the plunger arm.

39. A delivery device according to claim 38, the sensor configured to measure a linear force of the drive linkage, the linear force of the drive linkage corresponding to the force on the plunger arm.

40. A delivery device according to claim 38, wherein the force on the plunger arm is in a direction opposite a direction of movement of the plunger arm to deliver fluidic media from the reservoir.

41. A delivery device according to claim 38,
the drive linkage having a first gear operatively engaged with a second gear;
wherein the plunger arm and the first gear are arranged so that the force on the plunger arm applies a torque on the first gear; and
wherein the first gear and the second gear are arranged so that the torque on the first gear applies the linear force on the second gear.

42. A delivery device according to claim 41,
wherein the first gear comprises a worm gear; and
wherein the second gear comprises a worm.

43. A delivery device according to claim 41, the delivery device further comprising:
circuitry for controlling the drive device;
the first gear operatively engageable with the plunger arm to allow the drive device to move the plunger arm;
the circuitry configured to control the drive device to move at least one of the first gear and the second gear based on a measurement of the sensor.

44. A delivery device according to claim 43, the circuitry configured to control the drive device to move the first gear to reduce a rotational range of motion of the first gear relative to the plunger arm.

45. A delivery device according to claim 43, the circuitry configured to control the drive device to move the second gear to reduce a rotational range of motion of the first gear relative to the plunger arm.

46. A delivery device according to claim 45, the circuitry configured to control the drive device to move the second gear to reduce the rotational range of motion of the first gear relative to the plunger arm sufficiently to allow the drive device to move the plunger arm.

47. A delivery device according to claim 43, wherein the drive device is controlled to move at least one of the first gear and the second gear by the circuitry based on the force measured by the sensor.

48. A delivery device according to claim 43, wherein the drive device comprises an electrical motor.

49. A delivery device according to claim 38, wherein the sensor comprises a force sensor.

50. The delivery device of claim 38, wherein the drive linkage is arranged to exert the measured force on the sensor.

51. A method of making a delivery device for delivering fluidic media, the method device comprising:
  adapting a first housing portion to be secured to a user;
  configuring a second housing portion to be selectively engaged with and disengaged from the first housing portion, one of the first housing portion and the second housing portion for supporting a reservoir for containing fluidic media;
  configuring a drive device to be operatively engagable with a plunger arm connected to a plunger head arranged for movement by the drive device in an axial direction of the reservoir, the drive device configured to drive fluidic media from the reservoir in a case where the drive device is operatively engaged with the reservoir and the plunger arm is moved in the axial direction relative to the reservoir;
  providing a drive linkage for operatively engaging the drive device with the plunger arm to allow the drive device to move the plunger arm; and
  configuring a sensor to measure a force on the drive linkage corresponding to a force on the plunger arm.

* * * * *